(12) United States Patent
Kulkarni

(10) Patent No.: US 10,485,422 B2
(45) Date of Patent: Nov. 26, 2019

(54) SYSTEM AND METHOD FOR IMAGING SUBSURFACE OF SPECIMEN

(71) Applicant: Manish Dinkarrao Kulkarni, Pleasanton, CA (US)

(72) Inventor: Manish Dinkarrao Kulkarni, Pleasanton, CA (US)

( * ) Notice: Subject to any disclaimer, the term of this patent is extended or adjusted under 35 U.S.C. 154(b) by 639 days.

(21) Appl. No.: 13/723,006

(22) Filed: Dec. 20, 2012

(65) Prior Publication Data

US 2014/0180075 A1 Jun. 26, 2014
US 2016/0256051 A9 Sep. 8, 2016
US 2016/0367136 A9 Dec. 22, 2016

Related U.S. Application Data

(63) Continuation-in-part of application No. 12/732,484, filed on Mar. 26, 2010, now abandoned, and a continuation-in-part of application No. 12/706,717, filed on Feb. 17, 2010, now abandoned.

(60) Provisional application No. 61/163,872, filed on Mar. 27, 2009, provisional application No. 61/153,893, filed on Feb. 19, 2009.

(51) Int. Cl.
| | | |
|---|---|---|
| A61B 5/05 | (2006.01) | |
| A61B 3/12 | (2006.01) | |
| A61B 5/00 | (2006.01) | |
| A61B 3/10 | (2006.01) | |
| A61B 1/24 | (2006.01) | |

(Continued)

(52) U.S. Cl.
CPC .............. *A61B 3/1241* (2013.01); *A61B 1/24* (2013.01); *A61B 3/102* (2013.01); *A61B 3/12* (2013.01); *A61B 5/004* (2013.01); *A61B 5/0066* (2013.01); *A61B 5/0088* (2013.01); *A61B 5/02007* (2013.01); *A61B 5/08* (2013.01); *A61B 5/42* (2013.01); *A61B 5/7221* (2013.01); *A61B 5/7225* (2013.01)

(58) Field of Classification Search
None
See application file for complete search history.

(56) References Cited

U.S. PATENT DOCUMENTS 4,615,582 A 10/1986 Lefevre
5,994,690 A * 11/1999 Kulkarni .............. A61B 5/7257
250/216

(Continued)

OTHER PUBLICATIONS

D. Hillmann, G. Hüttmann, and P. Koch, "Using Nonequispaced Fast Fourier Transformation to Process Optical Coherence Tomography Signals," in Optical Coherence Tomography and Coherence Techniques IV, P. Anderson and B. Bouma, eds., vol. 7372 of Proceedings of SPIE—OSA Biomedical Optics (Optical Society of America, 2009), paper 7372_0R.*

(Continued)

*Primary Examiner* — Joel F Brutus

(57) ABSTRACT

There is a need for robust and portable system, apparatus and method for imaging subsurface of specimens. We have described a modular OCDR-OCT system and OFDR-OCT system to obtain high quality images. The instant application also discusses proprietary algorithms that have been modified from existing algorithms and their use as a combination to suit a particular system. The imaging of stationary, moving and combination of both subsurface structures such as retina for diabetic patients is described.

20 Claims, 13 Drawing Sheets

(51) Int. Cl.
A61B 5/02 (2006.01)
A61B 5/08 (2006.01)

(56) References Cited

U.S. PATENT DOCUMENTS

| | | | |
|---|---|---|---|
| 6,289,740 B1* | 9/2001 | Posey, Jr. | G01L 1/246 250/227.18 |
| 6,385,358 B1 | 5/2002 | Everett et al. | |
| 6,564,089 B2 | 5/2003 | Izatt et al. | |
| 7,126,693 B2 | 10/2006 | Everett et al. | |
| 7,995,207 B2 | 8/2011 | Podoleanu | |
| 2003/0103212 A1* | 6/2003 | Westphal et al. | 356/479 |
| 2004/0016874 A1* | 1/2004 | Rao et al. | 250/225 |
| 2004/0239943 A1* | 12/2004 | Izatt | G01N 21/4795 356/479 |
| 2005/0018133 A1* | 1/2005 | Huang | A61B 3/102 351/205 |
| 2005/0171438 A1* | 8/2005 | Chen | A61B 5/0066 600/476 |
| 2005/0174578 A1* | 8/2005 | Wei | A61B 3/102 356/477 |
| 2007/0195269 A1* | 8/2007 | Wei | A61B 3/102 351/221 |
| 2007/0229801 A1* | 10/2007 | Tearney | A61B 5/0062 356/73 |
| 2008/0204762 A1* | 8/2008 | Izatt | A61B 3/102 356/521 |
| 2010/0208270 A1 | 8/2010 | Kulkarni et al. | |
| 2010/0220334 A1* | 9/2010 | Condit et al. | 600/476 |
| 2010/0245836 A1 | 9/2010 | Kulkarni et al. | |
| 2011/0096291 A1* | 4/2011 | Buckland | A61B 3/102 351/206 |
| 2011/0273721 A1 | 11/2011 | Kulkarni et al. | |
| 2012/0138586 A1* | 6/2012 | Webster et al. | 219/121.64 |

OTHER PUBLICATIONS

Jianping Su, Jun Zhang, Lingfeng Yu, Henri G Colt, Matthew Brenner, and Zhongping Chen, "Real-time swept source optical coherence tomography imaging of the human airway using a microelectromechanical system endoscope and digital signal processor" Journal of Biomedical Optics, May/Jun. 2008, vol. 13(3), 030506-1.

Sebastien Vergnole, Daniel Levesque, and Guy Lamouche, "Experimental validation of an optimized signal processing method to handle non-linearity in swept-source optical coherence tomography", May 10, 2010 / vol. 18, No. 10 / Optics Express p. 10446.
Samuel C. Barden, James A. Arns, Willis S. Colburn and Joel B. Williams, "Volume—Phase Holographic Gratings and the Efficiency of Three Simple Volume—Phase Holographic Gratings," Publications of the Astronomical Society of the Pacific, vol. 112, No. 772 (Jun. 2000), pp. 809-820.
Jianping Su, Jun Zhang, Lingfeng Yu, Henri G Colt, Matthew Brenner, and Zhongping Chen, "Real-time swept source optical coherance tomography imaging of the human using a microelectromechanical system endoscope an digital signal processor", Journal of Biomedical Optics, May/Jun. 2008, vol. 13(3), 030506-1.
H. Lim, M. Muja, C. Kerbage, E. C. W. Lee, and Y. Chen, Teresa C. Chen, J. F. De Boer, "High-speed imaging of human retina in vivo with swept-source optical coherence tomography," Dec. 25, 2006, vol. 14, No. 26 / Optics Express 12902.
Michael A. Choma, Marinko V. Sarunic, Changhuei Yan, Josepha A. Izatt, "Sensitivity advantage of swept source and Fourier domain optical coherence tomography," Sep. 8, 2003 / vol. 11, No. 18 / Optics Express p. 2183.
H. Lim, J. F. De Boer, B. H. Park, E. C. W. Lee, R. Yelin, and S. H. Yun, "Optical frequency domain imaging with a rapidly swept laser in the 815-870 nm range," Jun. 26, 2006 / vol. 14, No. 13 / Optics Express 5937.
Benjamin Postsaid, Bernhard Baumann, David Huang, Scott Barry, Alex E. Cable,Joel S. Schuman, Jay S. Duker, and James G. Fujimoto, "Ultrahigh speed 1050nm swept source / Fourier domain OCT retinal and anterior segment imaging at 100,000 to 400,000 axial scans per second", Opt Express. Sep. 13, 2010; 18(19): 20029-20048.
Manish D Kulkarni, "Coherent Signal Processing in Optical Coherence Tomography" PhD Thesis Advisor: Prof. Joseph A. Izatt, Department of Biomedical Engineering, Case Western Reserve University, Cleveland, OH, Jan. 1999.
I. Hartl, X. D. Li, C. Chudoba, R. K. Ghanta, T. H. Ko, J. G. Fujimoto, J. K. Ranka and R. S. Windeler, "Ultrahigh-resolution optical coherence tomography using continuum generation in an air—silica microstructure optical fiber," Optics Letters / vol. 26, No. 9 / May 1, 2001, p. 608.
Jonathan E. Roth, Jennifer A. Kozak, Siavash Yazdanfar, Andrew M. Rollins, and Joseph A. Izatt, "Simplified method for polarization-sensitive optical coherence tomography," Optics Letters / vol. 26, No. 14 / Jul. 15, 2001, p. 1069.

* cited by examiner

SYSTEM AND METHOD FOR IMAGING SUBSURFACE OF SPECIMEN

CROSS REFERENCE TO RELATED APPLICATIONS

The instant application is a continuation-in-part application and claims priority to pending U.S. patent application Ser. No. 12/732,484, filed on 26 Mar. 2010 and U.S. patent application Ser. No. 12/706,717, filed on 17 Feb. 2010. The disclosure is hereby incorporated by this reference in its entirety for all of its teachings.

FIELD OF TECHNOLOGY

The following description relates to a system, method and an apparatus for imaging and evaluating the microstructure of any specimen on the subsurface. More specifically the description is relevant to imaging of biological specimen such as a retina in diabetic patients using optical coherence domain reflectometry (OCDR), optical frequency domain reflectometry (OFDR), optical coherence tomography (OCT), Doppler processing and Doppler OCT technology in combination.

BACKGROUND

Optical Coherence Domain Reflectometry (OCDR) has been playing a major role in industrial, scientific metrology and medical diagnostics. Optical Coherence Tomography (OCT) is a 2-D extension of OCDR and provides micron-resolution cross-sectional images of specimens. Most of the industrial and clinical OCDR, OFDR and OCT machines are disparate, expensive, cumbersome to use, bulky, not very efficient and are fragile. Everett et al. (2006) discusses these systems in isolation and in some combinations in detail.

However, a more compact and integrated system and an apparatus would make diagnosis more accurate and the apparatus more portable.

SUMMARY

The invention discloses a system, method and apparatus, for evaluating the retinal microstructure in diabetic patients and other substructure for failure analysis using optical coherence domain reflectometry (OCDR), optical frequency domain reflectometry (OFDR), optical coherence tomography (OCT), Doppler processing and Doppler OCT technology in combination.

In one embodiment, an apparatus comprises of a light source, isolator, beam splitter, optical delivery unit, specimen, volume-phase holographic grating unit, detector array and a processor containing novel algorithms for image processing. This is described as the basic configuration throughout the instant application with mirror addition and deletion of components. In another embodiment, the apparatus mentioned above has also at least one of a faraday rotator mirror, fractional wave mirror, waveplate (e.g., $\lambda/8$), a fiber-optic mirror and a free space mirror.

In another embodiment as an additional feature, a polarization compensator is added to the basic configuration mentioned above. In one embodiment, a fiber stretcher is added in the basic configuration. The fiber stretcher is used to adjust the path-length in the corresponding arm of the system.

In one embodiment, a system comprising of light source, provides a broad band light for acquiring an image from subsurface area of a specimen. The specimen may be, but not limited to a moving sample, a stationary sample or a combination of both. In another embodiment, the system is modular so that a user can add off-the-shelf products to enhance the system capabilities. In another embodiment, several combinations of the basic configuration and additional components may be added to enhance the performance of the apparatus as a system as shown in the various figures that accompany this application, but not limited to only those.

In another embodiment, a compensating algorithm resides in the processor to create a superior image. The processor uses the algorithms such as the frequency resampling, demodulation, dispersion compensation, and Doppler processing to produce highly sensitive and high quality images. In another embodiment, the system performs spectroscopic detection. The resultant spectra are analyzed by the processor using inverse Fourier transformation and relevant signal processing for obtaining depth dependent (i.e. axial) reflectivity profile called A-scan. In another embodiment, two dimensional tomographic images, B-scan, are created from a sequence of axial reflectance profiles acquired by scanning the specimen.

In one embodiment, a system may comprise of a light source, isolator, processor, fiber stretcher, source arm, reference arm, sample arm, detection arm, beam splitter, detector array, volume-phase holographic grating unit, optical delivery unit, $\lambda/8$ waveplate, fractional wave mirror and a specimen for analysis.

In another embodiment, the system comprises of a light source, isolator, processor, detector array, fiber stretcher, source arm, reference arm, sample arm, detection arm, beam splitter, volume-phase holographic grating unit, optical delivery unit, polarization compensator, mirror and a specimen for analysis.

In another embodiment, the system comprises of a light source, isolator, processor, detector array, fiber stretcher, source arm, reference arm, sample arm, detection arm, beam splitter, volume-phase holographic grating unit, optical delivery unit, polarization compensator and another optical delivery system located on the reference arm, free space mirror and a specimen for analysis.

In another embodiment, a system may comprise of a tunable light source, isolator, processor, fiber stretcher, source arm, reference arm, sample arm, detection arm, beam splitter, detector, optical delivery unit, $\lambda/8$ waveplate, fractional wave mirror and a specimen for analysis.

In another embodiment, the system comprises of a light source, isolator, processor, detector array, fiber stretcher, source arm, reference arm, sample arm, detection arm, beam splitter, volume-phase holographic grating unit, optical delivery unit, polarization compensator located on the sample arm, fractional wave mirror and a specimen for analysis.

In one embodiment, a system may comprise of a light source, isolator, processor, fiber stretcher, source arm, reference arm, sample arm, detection arm, beam splitter, detector array, volume-phase holographic grating unit, optical delivery unit, $\lambda/8$ waveplate, faraday rotator mirror and a specimen for analysis.

In one embodiment, a system may comprise of a tunable light source, isolator, processor, fiber stretcher, source arm, reference arm, sample arm, detection arm, beam splitter, detector, optical delivery unit, $\lambda/8$ waveplate, faraday rotator mirror and a specimen for analysis.

In another embodiment, the system comprises of a light source, isolator, processor, detector array, fiber stretcher, source arm, reference arm, sample arm, detection arm, beam splitter, volume-phase holographic grating unit, optical delivery unit, polarization compensator located on the sample arm, faraday rotator mirror and a specimen for analysis.

In another embodiment, the system enables a user to adjust the reference arm and the sample arm in order to adjust the variance of the light beam to get a better quality image.

In one embodiment, a method of acquiring sensitive, high quality image of the subsurface for diagnostics and failure analysis is described.

In another embodiment, light from a broadband light source operating at a suitable center wavelength is sent to an isolator, and then to the beam splitter using the source arm of the apparatus. In another embodiment, the beam splitter splits the broadband light into two parts. One part of the light beam goes to the reference mirror using the fiber stretcher (on the reference arm) and other beam goes to the specimen using the sample arm.

In another embodiment, the reflected light from the mirror using the reference arm joins the light reflected from the specimen using the sample arm. In another embodiment, the combined light from the reference arm and sample arm is split again at the beam splitter and part of the beam goes back to isolator. The other part of the beam goes to the VPH (volume-phase-holographic grating unit) and detector array using the detector arm. The beam then is transformed using novel algorithms that are discussed in detailed description and transformed to produce high quality, sensitive images. In another embodiment, if the image quality is poor then the whole process is repeated, the user is given the option to adjust the reference arm length, adjust the polarization using polarization compensation, or focus the light using optical delivery unit to further improve the image.

In one embodiment the apparatus comprising of many components and systems is modular. In another embodiment the processor/computer-readable media houses the novel algorithm to process the beam that has the spectrophotometric image information of the specimen.

In one embodiment, a method to process the acquired image using several types of systems using the algorithms residing in the computer-readable media is described.

The above mentioned summary presents a simplified version of one or more embodiments in order to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later. Other aspects will be apparent from the following description, figures and the appended claims.

Other features of the present embodiments will be apparent from the accompanying figures and from the detailed description that follows.

DETAILED DESCRIPTION

The instant disclosure describes a technological advancement of acquiring an image that is stationary, moving and/or combination of stationary and moving specimen in subsurface area and enhancing the quality of the image by using proprietary algorithms. The disclosure also describes an apparatus, a system and a method for evaluating the retinal microstructure in diabetic patients and other substructure for failure analysis using optical coherence domain reflectometry (OCDR), optical frequency domain reflectometry (OFDR), optical coherence tomography (OCT), Doppler processing and Doppler OCT technology in combination.

Figure 1:
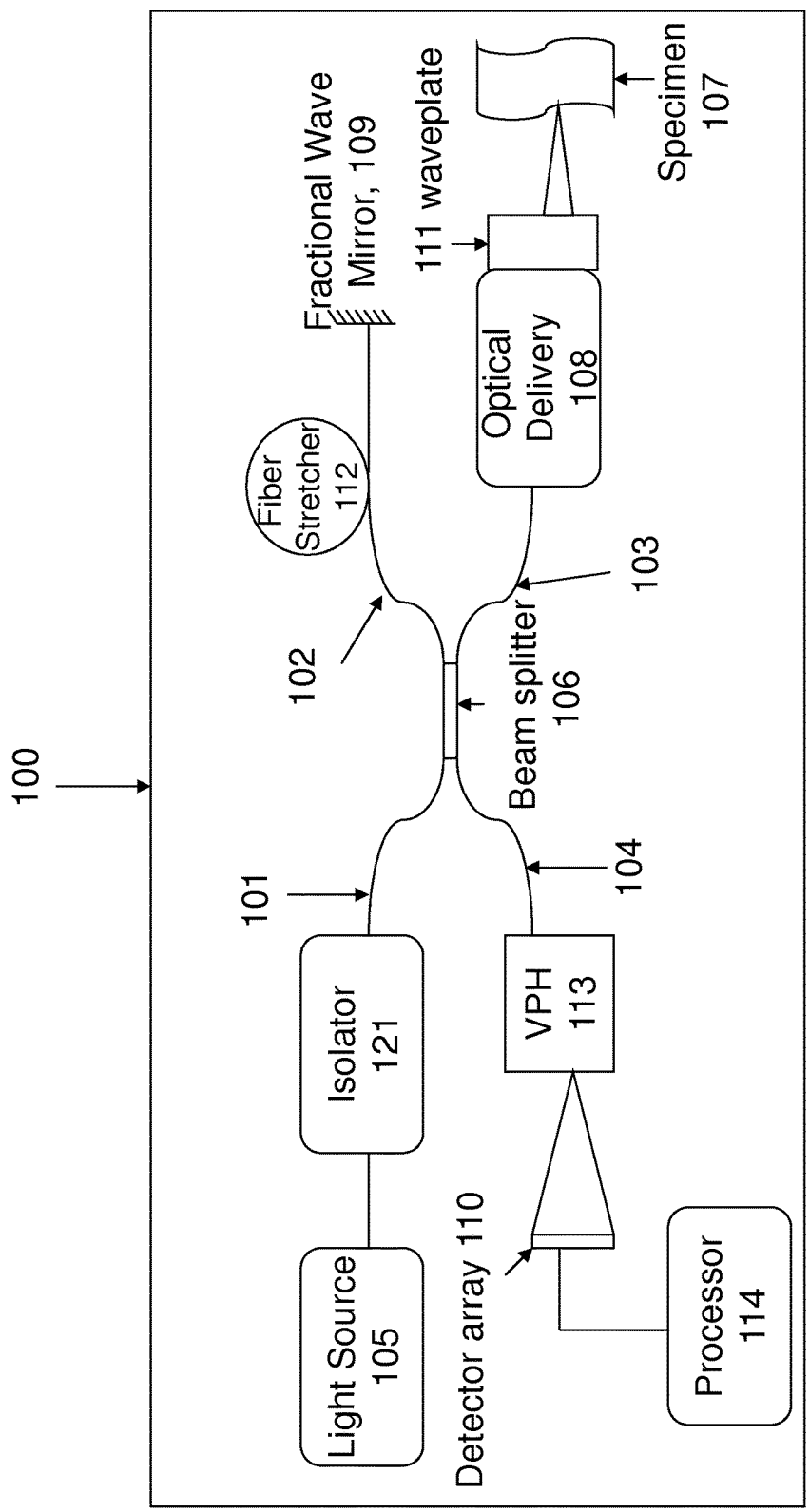
FIG. 1 is a block diagram of an OCDR-OCT system 100, in accordance with an embodiment of the present invention; the key novel elements being volume phase holographic grating unit, fiber optic Fractional Wave mirror, fiber stretcher, and λ/8 waveplate.

OCDR-OCT System: FIG. 1 shows an OCDR-OCT system 100 comprising of a light source 105, isolator 121, processor 114, fiber stretcher 112, source arm 101, reference arm 102, sample arm 103, detection arm 104, beam splitter 106, detector array 110, volume-phase holographic grating unit 113, optical delivery unit 108, λ/8 plate 111, Fractional wave mirror 109 and a specimen 107 for analysis. This is one of the preferred embodiments for our invention.

A light source 105, in a system or as a part of the apparatus, may comprise of off-the-shelf light sources.

The center wavelength ($\lambda_0$) most ideal for the retinal applications range from 750 nm till 1050 nm. Water (and aqueous humor) absorption is minimal for this wavelength range. The power for retinal applications ranges from 0.1 mW to 10 mW. Per ANSI safety standards only 0.75 mW are permitted incident on the eye at this wavelength range of 750 nm till 1050 nm. The center wavelength most ideal for the non-retinal applications (e.g., skin, anterior segment of the eye, gastrointestinal tract, lungs, teeth, blood vessels, subsurface area of semi-conductors, chip manufacturing, sensitive medical equipment's etc.) range from 1050 nm till 1350 nm. The longer wavelength is more suitable for thick scattering tissues since scattering is less at higher wavelengths. The system depth resolution (DR) is inversely proportional to the FWHM spectral width (or bandwidth$\Delta\lambda$). It is given by the following equation:

$$DR = \frac{2\ln 2}{\pi} \frac{\lambda_0^2}{\Delta\lambda} \quad \text{(Eq 1)}$$

The full-width-half-max (FWHM) spectral width of the light source typically ranges from 10 nm till 150 nm. The power for non-retinal applications ranges from 0.1 mW till 30 mW in the wavelength range from 1050 nm till 1350 nm. The full-width-half-max (FWHM) spectral width of the light source typically ranges from 10 nm till 150 nm.

The light source 105 may be electrically operated. These can be battery operated while in transit. The forward voltage typically ranges from 2 to 10 Volts. The forward current typically ranges from 100 mA to 1 A. Some of these sources need to be thermo-electrically controlled (TEC). The operating internal temperature for some sources is typically 25° C. The corresponding thermistor resistance is 10 kilo-Ohms (10 k$\Omega$). Typical TEC current is 1.5 A. Typical TEC voltage is 3-4V. The light source may also be tunable light source as shown in other system/apparatus embodiments.

The isolator 121 protects the light source from back reflections and permits the transmission of light in the forward direction with a limited loss. The fiber-optic isolator used in idevice would need to operate on a broad range of spectrum to cover the full spectral-width of the light source (Depending upon the source spectral shape, typically 2*FWHM bandwidth $\Delta\lambda$). Thus the operating wavelength range is $\lambda_0$+/-$\Delta\lambda$. Typical isolation is 20-40 dB, and insertion loss is 0.5-3 dB. The polarization dependent loss is typically 0.5 dB or less. Return loss is typically more than 40 dB.

The isolator 121 comprises of an input linear polarizer, a ($\lambda$/8) Faraday rotator or a waveplate, and an output linear polarizer. The ($\lambda$/8) Faraday rotator or a waveplate rotates the light transmitted through the input polarizer by 45 degrees. The output polarizer needs to have the same direction as "the input polarizing direction rotated by 45 degrees" in order to have the maximum transmission and maximum isolation. The light returning to the isolator from the remaining system gets linearly polarized by the output polarizer and is rotated by 45 degrees, making it orthogonally polarized as compared to the input polarizing direction. Thus, the returning light is totally absorbed.

Fiber stretcher 112 consists of a fiber looped around a piezoelectric device (which is a solid block that can be expanded or contracted by electric voltage). The purpose of a fiber stretcher is to increase or decrease the path-length in the interferometer that is on the detection arm by increasing or decreasing the fiber-length. Although the fiber stretcher 112 is shown in the reference arm, it can be placed ether in the reference arm or sample arm. If the fiber stretcher 112 is kept in the reference arm, since the fiber is looped around the piezoelectric device, care must be taken to provide extra fiber in the sample arm so that the sample arm and reference arm path lengths are matched.

The fractional wave mirror 109 consists of a fiber-optic mirror preceded by a fractional [45 degrees ($\lambda$/8)] waveplate. The polarization of light incident on the wave plate is rotated by 45 degrees, and is directed to the mirror. The reflected light is further rotated by 45 degrees by the fractional [45 degrees ($\lambda$/8)] waveplate and hence the resulting polarization is orthogonal to the incident polarization. We would use a fiber optically integrated birefringent reference mirror is at least one of fractional wave mirror, mirror, free space mirror and Faraday rotator mirror. A modified formula based on LeFvre is disclosed in this disclosure and which is as follows:

Mechanical stress on the fiber is causes birefringence in the fiber. Stress can be generated by simply bending the fiber. According to LeFevre (U.S. Pat. No. 4,615,582), the fractional wave plate can be built by looping the fiber into N loops having a radius R. The refractive index difference $\Delta n$ for two orthogonal polarizations is given by $$\Delta n = b\left(\frac{r}{R}\right)^2 \quad \text{(Eq 2)}$$

b is a constant depending upon the photoelastic coefficient of the fiber, r is the radius of the fiber and R is the radius of the fiber loop. Thus, if we want to create a $\lambda$/m (where m is an integer) waveplate, which will introduce a path-length shift of $\lambda$/m between 2 polarizations, we'll need to create a loop of fiber length L to create the path-length shift of $\Delta$nL. However, since the length of the fiber is also equal to $2\pi NR$, where N is the number of loops, we get $$(2\pi NR)b\left(\frac{r}{R}\right)^2 = \frac{\lambda}{m} \quad \text{(Eq 2)}$$

or $$R = (2\pi mN)b\frac{r^2}{\lambda} \quad \text{(Eq 4)}$$

To create a fractional wave plate of $$\frac{\lambda}{8},$$

and N=1 (single loop), b=0.25, m=8, r=125 microns, $\lambda$=0.8 microns, we get $$R = (2\pi 8)0.25\frac{(125)^2}{0.8} = 5\pi * 15625 = 24.54 \text{cm} \quad \text{(Eq 5)}$$

Please note that a (2M+1)$\lambda$/m waveplate where M is an integer between $-\infty$ to $\infty$ will have a similar effect as a $\lambda$/m waveplate.

In typical state-of-the-art OCT systems, light exits a fiber tip in the reference arm and the light returns from a retro reflecting mirror mounted in air. This increases system complexity and bulkiness. In some embodiments of instantly described invention, a fiber-optically integrated fractional wave mirror 109 in the reference arm 102 of the OCDR-OCT system 100 can be used. Since the polarization of the retro reflected light is orthogonal to the incident light, fiber birefringence effects effectively get cancelled in the reference arm 102.

Detector array 110 is a line-scan camera. It has typically 1024-4096 pixels, though the proposed embodiment is not limited to these numbers. Typically it is a CCD or CMOS camera. Line-rate (rate of acquisition of arrays) is typically 10000 lines/s to 400000 lines/s, though the proposed embodiment is not limited to these numbers. Each pixel outputs a value which typically has an 8-bit or 12-bit format, though the proposed embodiment is not limited to these numbers. The pixel size is typically 14 microns (height) and 14 microns (width). The light dispersed by the grating is focused on the detector array. The output of the array (line-scan camera) is typically directed to the computer using an Ethernet cable (e.g., Gigabit Ethernet) or a USB (typically 2.0 or 3.0) cable, etc. The operating wavelength ranges from 400 nm to 1100 nm for retinal applications. The above numbers and examples are given for illustrative purposes only, the proposed embodiment is not limited to these numbers or examples.

The beam splitter 106 (made of fiber optics) splits the light typically into 50/50. It is built using two fused single-mode fibers. The fiber for retinal applications (~800 nm wavelength) has 4-6 microns core diameter and 125 microns cladding diameter, 0.130 core numerical aperture (NA), cutoff wavelength of typically 730 nm. The insertion loss (in addition to designed 3 dB or 50% loss) is typically 0.3 dB. For the couplers used for OCT, the length of the fiber in the reference and sample arms is very important and the lengths are specified with tight tolerances.

The waves reflected back from the sample arm 103 and the reference arm 102 interferes at the detector array 110. Since the interference signal is only created when the polarization in the reference arm 102 matches with that in the sample arm 103, in some embodiments, one can include by way of example but not by limitation a 45 degrees $\lambda/8$ waveplate 111 in the sample arm 103 just before the light is incident on the optical delivery unit 108. Since the polarization of the retro reflected light will be almost orthogonal to the incident light (considering the fact that the birefringence in the specimen 107 will modify the polarization state), the birefringence effects in the sample arm fiber 103 of the interferometer 100 will get cancelled. In a preferred embodiment, the $\lambda/8$ waveplate 111 is constructed using fiber optic components.

In an embodiment of this invention, other waveplates (non-45 degrees Faraday rotators) can be used. The quality of the interferometric signal (e.g., contrast and signal to noise ratio) will be better or worse depending upon the polarization properties of the specimen in the sample arm.

The instant system and apparatus that comprises of Optical coherence tomography (OCT) and OCDR that is very similar to ultrasound imaging. OCDR-OCT provides cross-sectional images of micro-features that are acquired from adjacent depth resolved reflectivity profiles of the tissue. OCT also employs a fiber optically integrated Michelson interferometer illuminated with a short coherence length light source such as a superluminiscent diode (SLD). The interferometric data are processed in a processor/computer and displayed as a gray scale image. In an OCDR-OCT image, the detectable intensities of the light reflected from human tissues range from $10^{-5}$ to $10^{-11}$th part of the incident power.

OCDR-OCT system 100 and OFDR-OCT 415 are able to image sub-surface retinal microstructure and has been useful for diagnosis and management of diabetic retinopathy. Abnormalities in blood-flow circulation due to diabetes are the root cause behind retinal microstructure damage. However, no clinical tools exist that can perform functional and velocity mapping of blood vessels in the retina for tracking early development of diabetic eye diseases. Therefore, there is a need for an automated, low-cost and compact tool based on Doppler OCT for tracking progression and management of diabetic retinal diseases by performing 3-D functional mapping of blood circulation in the retina. Such a device will be extremely useful in detecting earliest signs of diabetic retinopathy and hence it will be an ideal tool for screening diabetic patients at risk of developing retinopathy. Since it has been proven that glucose and blood-pressure control are the best methods for managing diabetic retinopathy, instant Doppler OCT system will be an ideal low-cost tool, which will permit screening as well as management for the disease. The invention presented here provides such a system and addresses these issues.

In another preferred embodiment, the $\lambda/8$ waveplate 111 is a fractional-waveplate constructed using fiber optic components. It would be constructed in the optical delivery unit near the end of the fiber segment in the optical delivery unit. Fractional waveplate 111 is located on the sample arm of the apparatus. It may be made an integral part of the optical delivery 108. The fractional wave mirror 109 consists of a fiber-optic mirror preceded by a fractional [45 degrees ($\lambda/8$)] waveplate. The polarization of light incident on the waveplate is rotated by 45 degrees, and is directed to the mirror. The reflected light is further rotated by 45 degrees by the fractional [45 degrees ($\lambda/8$)] waveplate and hence the resulting polarization is orthogonal to the incident polarization. In another embodiment, a free-space-bulk 45 degrees ($\lambda/8$) wave plate is used at the end of the optical delivery unit.

Instant OCDR-OCT system uses spectroscopic detection method. Basically the interferometric light exiting the detector arm 103 is dispersed via a grating. The spectra are acquired using a line-scan camera. The resulting spectra are typically (by way of example, not by limitation) transferred to a processor for inverse Fourier transforming and relevant signal processing (such as obtaining the complex envelope of the interferometric signal) for obtaining depth dependent (i.e., axial) reflectivity profiles (A-scans). The axial resolution is governed by the source coherence length, typically ~3-10 µm. Two dimensional tomographic images (B-scans) are created from a sequence of axial reflectance profiles acquired while scanning the probe beam laterally across the specimen or biological tissue.

A-scan: A-scan is a plot of reflectivity of scatterers and layers as a function of depth at a given lateral location. It is computed as follows:

a) The interferometric light exiting the detector arm is dispersed via a grating.
b) The dispersed light is a spectrum which is focused on a detector array or a line-scan camera.
c) The recorded spectra are typically transferred to a processor
d) An inverse Fourier transform of the spectrum is computed
e) Relevant signal processing is performed (such as removing the duplicate data and strong spikes at the center of the inverse Fourier transform)
f) The resulting arrays is a depth dependent (i.e., axial) reflectivity profiles (A-scans).
g) The axial resolution is governed by the source coherence length, typically ~3-10 µm.

Figure 11:
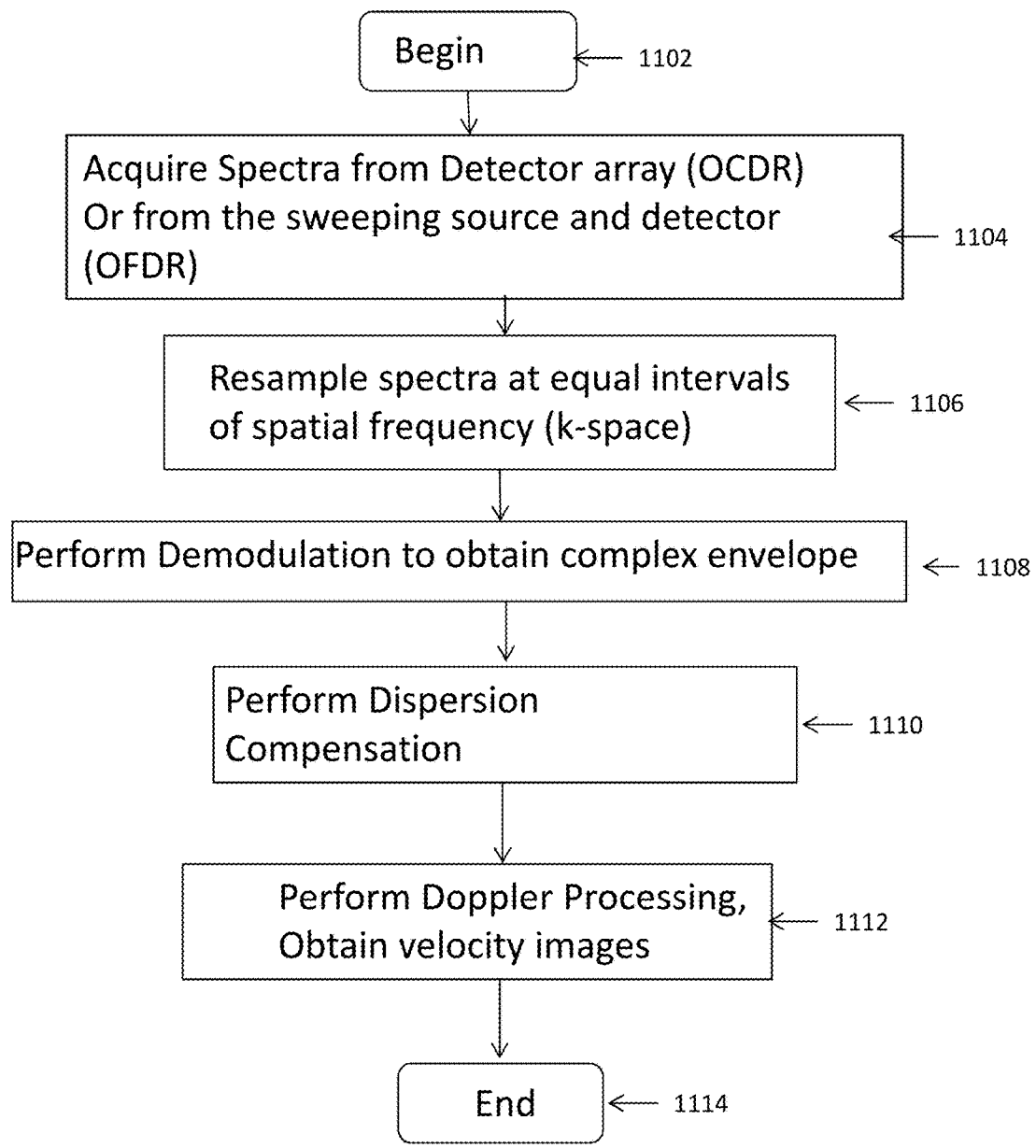
FIG. 11 is a flow chart of overview of methods of the signals and images being processed from the start to finish.
Figure 12:
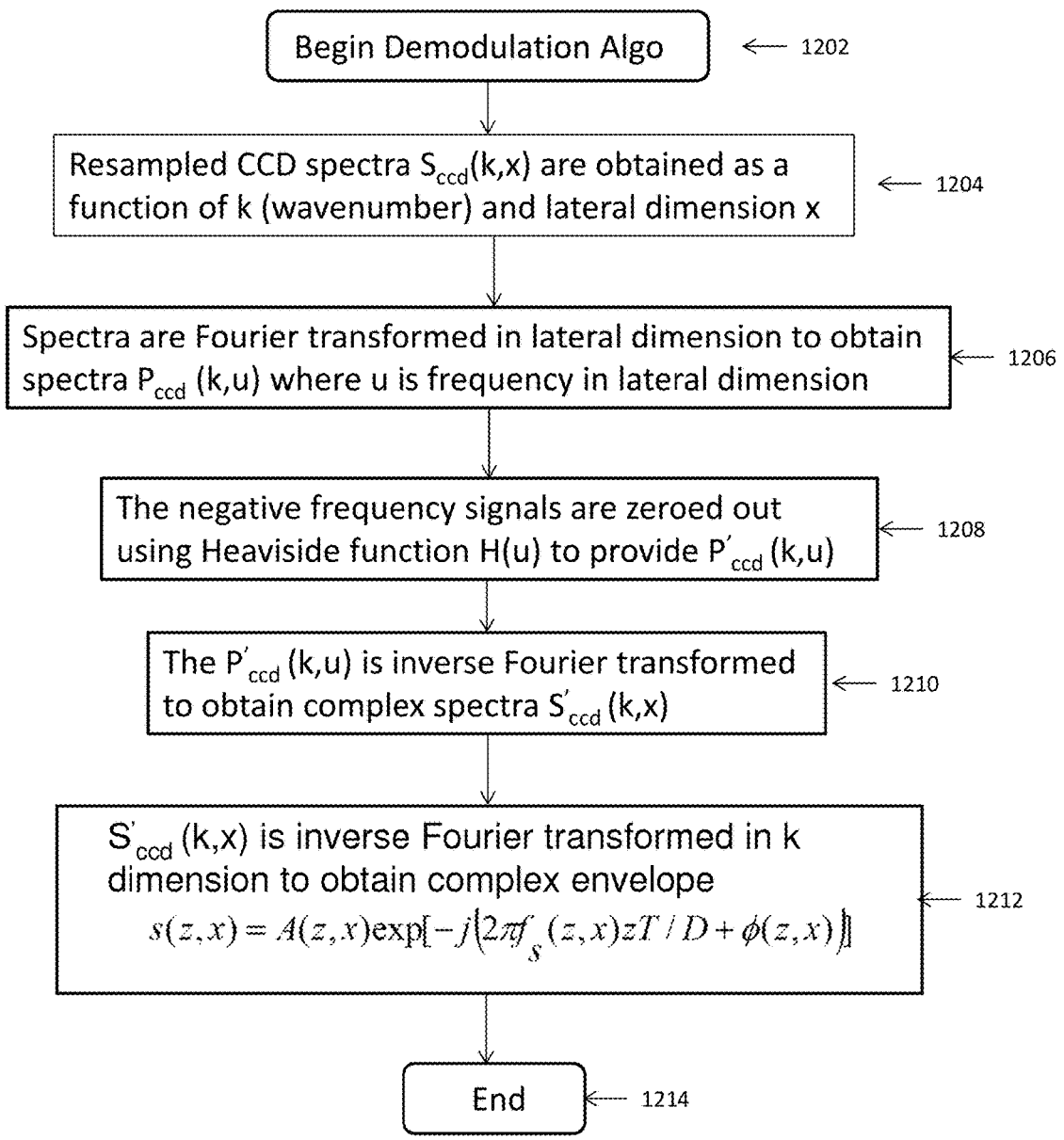
FIG. 12 is a flow chart of method of demodulating the signal to recover the complex envelope of the OCT/OCDR/OFDR signal.
Figure 13:
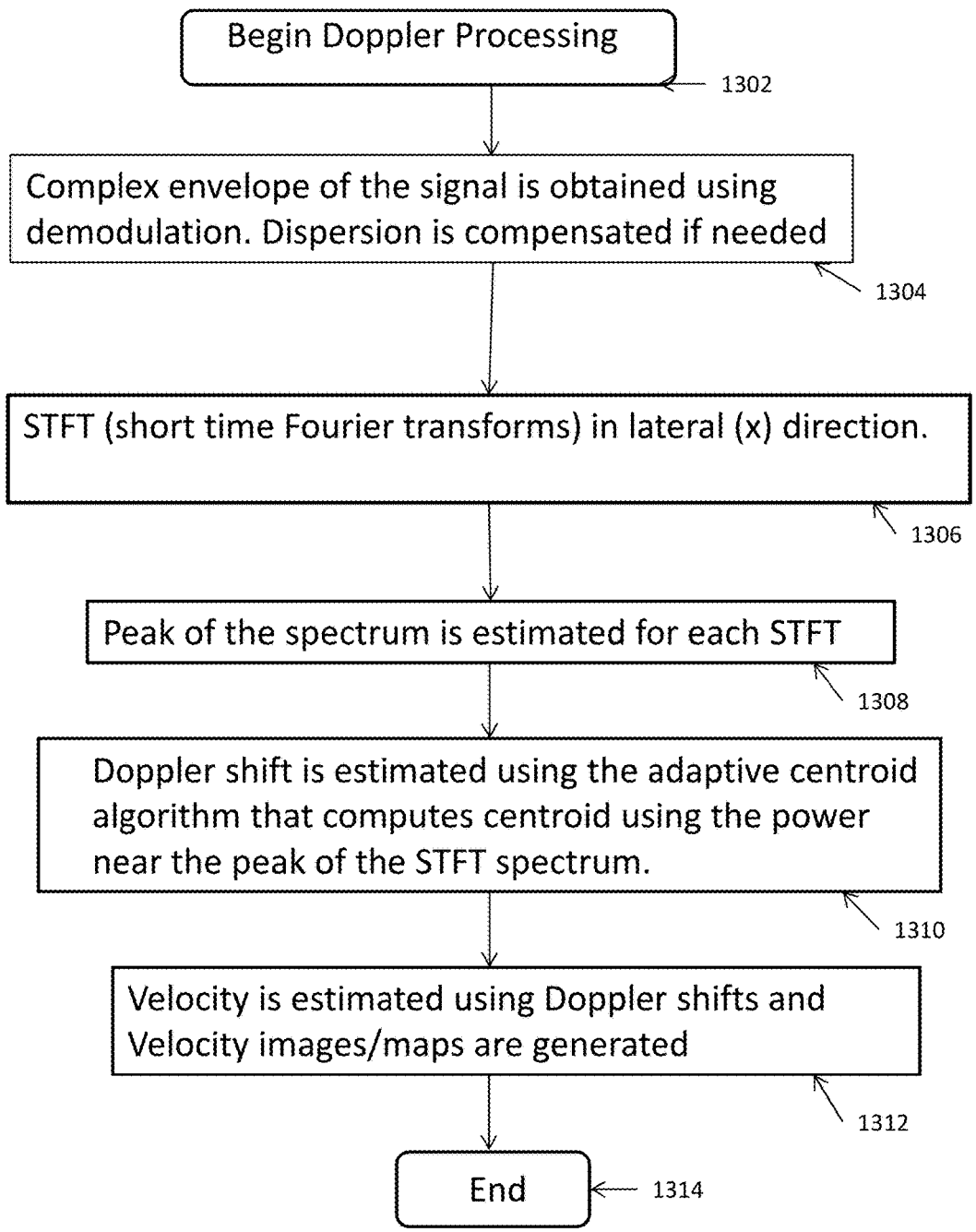
FIG. 13 is a flow chart of method of Doppler processing the signal to estimate the Doppler shift and the corresponding velocities of the particles in the specimen.

B-scan: Two dimensional tomographic images (B-scans) are created from a sequence of axial reflectance profiles acquired while scanning the probe beam laterally across the specimen or biological tissue. The following are detail steps:
a) An A-scan is acquired at a given lateral location.
b) A mirror is scanned using a scanner such as a galvanometer in the optical delivery unit
c) Multiple A-scans are acquired at various lateral locations.
d) A matrix is generated where columns indicate different lateral locations and rows indicate reflectivity at each depth in each A-scan
e) The matrix is displayed as an image, which is also a B-scan Processor comprises of many algorithms that are discussed below. There may be a combination of algorithms that may be used for image formation. The algorithms may be used individually or in certain sets, or in a serial manner. FIGS. 11, 12 and 13 discuss some embodiments, but the use is not limited to that only.

Dispersion compensation is an algorithm used in the instant invention. Dispersion is caused by mismatch in the materials in the reference and sample arms. In many situations, light may travel through more fiber in the reference arm and more air in the sample arm. This is especially possible if we use a fiber-optic mirror, which would result in no air in the reference arm. There would be some air in the sample arm as light needs to travel through optical delivery unit and focus on the specimen. The result of dispersion is loss of resolution and distortion of signal in the A-scan. Hence it needs to be corrected using dispersion algorithm. The corrected signal will have better depth resolution and higher fidelity.

Figure 5:
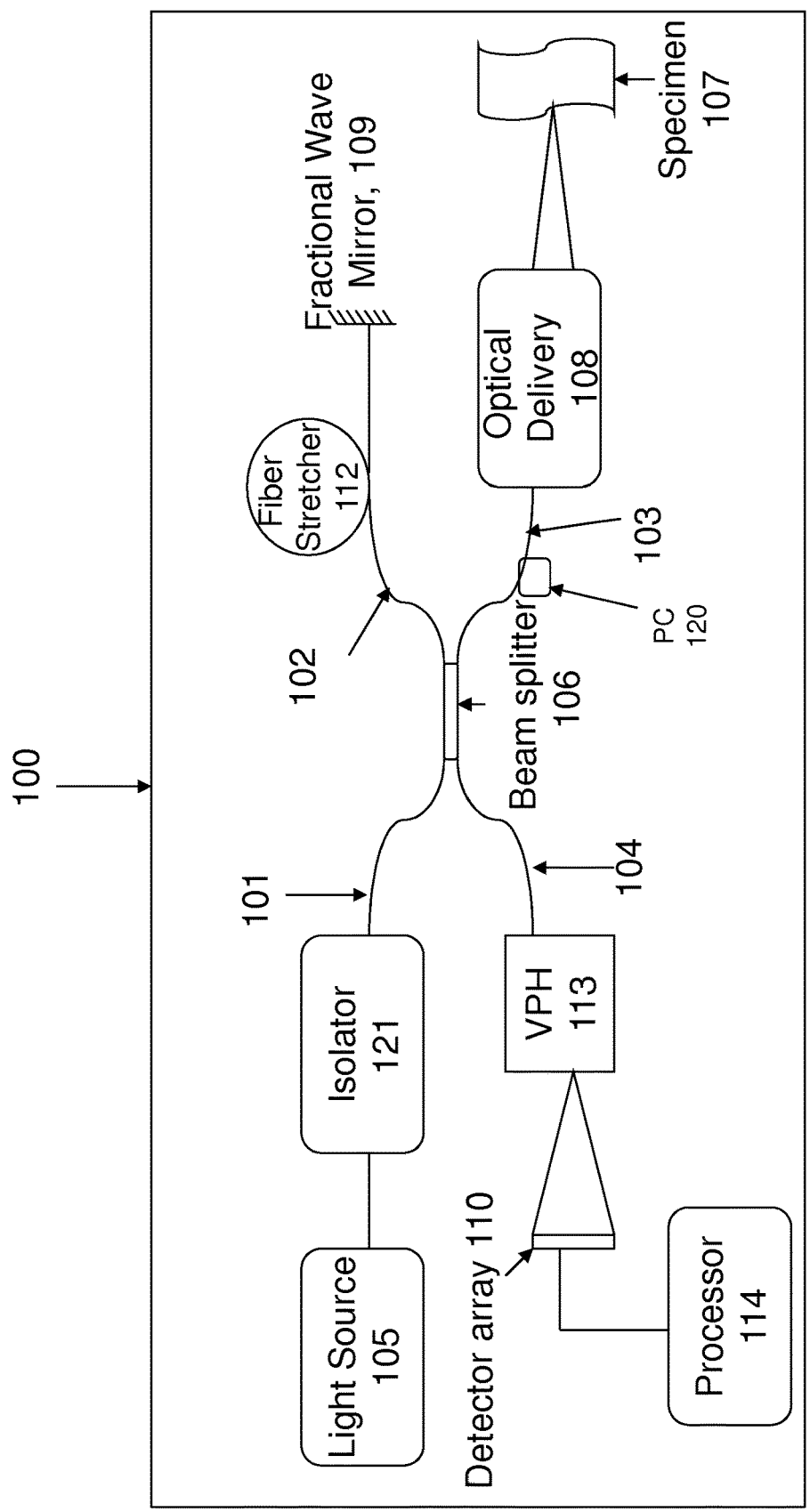
FIG. 5 is a block diagram of the OCDR-OCT system 100 similar to that in FIG. 1 except the λ/8 waveplate is eliminated and a polarization compensator is introduced in the sample arm.

In some embodiments, another way of achieving the polarization matching is to use a polarization compensator 220 as shown in FIG. 5 instead of using λ/8 waveplate 111. In other embodiments, combinations of waveplates and polarization compensators can be used to achieve the desired polarization matching. The prior art the control for the fiber optic polarization interferometer does not specify the precise location of the fiber-optic wave-plates along the reference or sample arm.

In the prior art, OCT systems need to dynamically adjust polarization (before each patient exam) in the sample arm 103 in order to match with polarization in the reference arm. We will not need dynamic polarization compensation due to instantly described novel approach.

TABLE 1

Advantages of Faraday rotator mirror

| Sr. No. | Faraday Rotator mirror advantage compared to mirror mounted in air | Implications for OCT-OCDR |
|---|---|---|
| [1] | Polarization effects get cancelled due to the orthogonal polarization of the retroreflected light | Polarization insensitivity, no need for dynamic compensation |
| [2] | Easy to assemble, no alignment needed in the reference arm | Low cost of production |
| [3] | Integral Part of the 3-dB coupler and reference arm assembly (wherein the same fiber is used to build the fiber optic splitter and the Faraday rotator mirror in the reference arm fiber.) | Robust, rugged, compact, low-cost |

Volume-Phase Holographic (VPH) Gratings: In the prior art, clinical OCT systems use ruled gratings for dispersing light on a line-scan camera in the detector arm. Ruled gratings are cumbersome and expensive. In some embodiments of currently described embodiment, volume-phase holographic (VPH) grating unit 113, which is essentially a transmission grating with alternating refractive indices, can be used. VPH grating unit are highly efficient, compact, rugged, and low-cost at telecom wavelengths since these are widely used in telecom industry. VPH grating unit were first developed for astronomy applications. The benefits of VPH grating unit are explained as follows (Table 2):

TABLE 2

Advantages of VPH grating unit:

| Sr. No. | VPH grating advantage compared to ruled grating | Implications for OCT and OCDR |
|---|---|---|
| [1] | have very high diffraction efficiency approaching 100%. | high sensitivity |
| [2] | Polarization effects are not as bad as in ruled gratings, | high sensitivity |
| [3] | lack many anomalies apparent in ruled gratings. | High image quality |
| [4] | Ghosting and scattered light from a VPH grating is substantially reduced compared to ruled gratings. | high sensitivity |
| [5] | Can be tuned to shift the diffraction efficiency peak to a desired wavelength. | high sensitivity |
| [6] | Can be tuned to direct more energy into higher diffraction orders using non-sinusoidal refractive index modulation on the grating (Barden et al. 2000); a versatility not possible with classical gratings. | high sensitivity |
| [7] | have high line densities (<6000 lines/mm) than ruled gratings at a lower cost | Higher scan depth, lower cost |
| [8] | can be cleaned due to the encapsulated nature of the grating. | More life, lower cost, higher sensitivity |
| [9] | The encapsulated nature permits antireflection coatings on the surfaces of the grating. | lower cost, higher sensitivity |
| [10] | can be designed to work in the Littrow configuration (as described in (Barden et al. 2000), where the fringe structure is normal to the grating surface, and the grating will have no | Lower cost to manufacture |

TABLE 2-continued

Advantages of VPH grating unit:

| Sr. No. | VPH grating advantage compared to ruled grating | Implications for OCT and OCDR |
|---|---|---|
|  | anamorphic magnification at the Bragg wavelength), resulting in a simplification of the line-scan camera objective optics (auto-collimated entrance and exit beams and the same focal length objectives can be used). |  |

In some embodiments of this invention, the grating disperses light and a lens focuses it into a detector array 110. By way of example, but not by limitation, this array can be a line-scan camera, which has quantum efficiency p at the operating wavelengths. The resulting data set is inverse Fourier transformed, processed in a processor 114 and displayed as a gray scale or pseudo-color image. By way of example, not by limitation, this processor can be a computer, off-the-shelf integrated circuit, Field application specific integrated circuit (ASIC), Programmable Gate Array (FPGA), a graphical processing unit (GPU) an embedded system or a microcontroller.

TABLE 3

Advantages of fiber optic waveplate coupled at the end of the fiber in the optical delivery unit

| Sr. No. | Fiber optic waveplate coupled at the end of the fiber in the optical delivery unit | Implications for OCDR-OCT |
|---|---|---|
| [4] | Polarization effects get cancelled due to the orthogonal polarization of the light backscattered from the sample | Polarization insensitivity, no need for dynamic compensation |
| [5] | Easy to assemble, no alignment needed in the sample arm | Low cost of production |
| [6] | Part of the 3-dB coupler and sample arm assembly | Robust, rugged, compact, low-cost |

TABLE 4

Advantages of fiber optic waveplate coupled before the optical delivery unit verses placing the waveplate before the sample

| Sr. No. | Fiber optic waveplate coupled before the optical delivery unit | Placing the waveplate before the sample |
|---|---|---|
| [7] | Robust, rugged, compact, low-cost | Fragile, bulk, expensive |
| [8] | Easy to assemble, no alignment needed in the sample arm | Hard to assemble, alignment needed in sample arm |
| [9] | Part of the 3-dB coupler and sample arm assembly | Part of the optical delivery unit |

$\lambda)k=1/\lambda)\delta\lambda=(\lambda max-\lambda min)/Nkmax=1/\lambda minkmin=1/kmax\delta k=(kmax-kmin)/N\delta k=(kmax-kmin)/XNS_{ccd}(k_0)=S_{ccd}(k_l)+U_0[S_{ccd}(k_u)-S_{ccd}(k_l)];$ $$U_0 = \frac{k_0 - k_l}{k_u - k_l} S_{ccd}(k_l) = W_{ccd}(\lambda_l, x) S_{ccd}(k_u) = W_{ccd}(\lambda_u, x)$$

Figure 2:
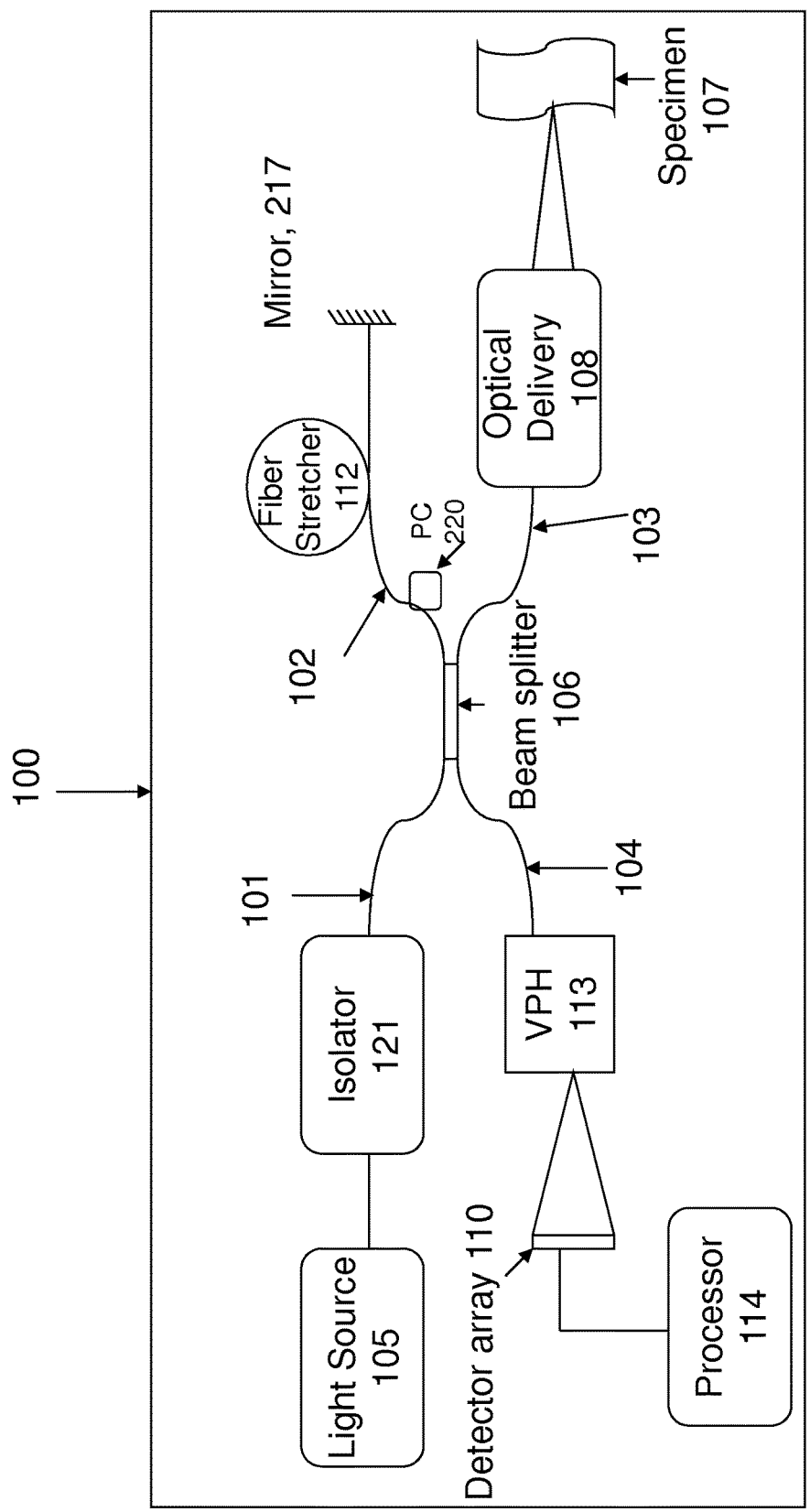
FIG. 2 is a block diagram of the OCDR-OCT system 100 similar to that in FIG. 1 except that the Fractional Wave mirror is replaced by a fiber optically integrated mirror, and the λ/8 waveplate is eliminated and a polarization compensator is introduced.

Alternate embodiments of instantly described OCT-OCDR system invention:

FIG. 2 is a block diagram of a system similar to that in FIG. 1 except that the Fractional Wave mirror is replaced by a fiber optically integrated mirror 217, and the (λ/8)th waveplate is eliminated and a polarization compensator 220 is introduced. FIG. 2 has standard fiber-optic-mirror in the reference arm, which still permits use of novel algorithms such as frequency resampling, demodulation, dispersion compensation, and Doppler processing algorithms. Polarization compensator 220 is also known as Fiber optic polarization compensators. These are based on the principles of fractional wave plate above. It consists of 3 coils of fiber on 3 different paddles arranged in a series. The first fiber coil is a quarter wave plate, the second fiber coil is a half wave plate (typically the fiber is looped around twice for the same paddle diameter as the first paddle), the last fiber coil is a quarter wave plate. These 3 paddles can be rotated freely with respect to each other to produce any polarization state.

There is another type of polarization compensator, which applies pressure to the fiber to create birefringence. The slow axis is in the direction of the pressure applied. This fiber squeezer can be rotated around the fiber to rotate the direction of the slow axis. Thus, any arbitrary polarization can be created.

Different types of gratings: Volume-Phase Holographic 113 grating unit is a transmission grating and the diffraction is achieved by periodic modulation of the refractive index. A similar effect could be achieved by periodic modulation of grating substrate thickness instead of (or in addition to) refractive index modulation.

Extensions of the proposed interferometer: An interferometric 2D imaging system (Optical coherence tomography or OCT) can be constructed using the proposed interferometric system where the 2D images are obtained by laterally scanning the beam incident on the sample using a 1-D scanning mirror (which is a part of the optical delivery unit). An interferometric 3D imaging system can be constructed using the proposed interferometric system where the 3D data-sets are obtained by 2D laterally scanning the beam incident on the sample using a 2-D scanning mirror (which is a part of the optical delivery unit).

Both the 2D imaging systems and 3D imaging systems can be adapted for ophthalmic imaging by using a lens assembly (which is a part of the optical delivery unit) to focus the light on the retina.

Both the 2D imaging systems and 3D imaging systems can be adapted for an endoscopic or catheter imaging system where the light in the sample arm is delivered through an endoscope. Thus, the sample arm fiber passes through an endoscope or a catheter. An example endoscopic OCT is shown in reference 4 (not as a limitation), but other endoscopic/catheter systems could be used.

TABLE 5

Advantages of instantly described proposed OCDR-OCT system:

| Sr. No. | Proposed feature in instant retinal OCT machine | Advantage to clinician and patient | State-of-the-art clinical retinal OCT machines |
|---|---|---|---|
| [1] | Scalable, price goes down with increasing sales volume due to use of device and packaging technologies | Increased affordability with device adaptation | Price does not go down with increasing sales volume due to use of labor intensive bulk technologies. |
| [2] | Portable | Can be easily transported to remote localities | Not portable |
| [3] | Rugged and Robust | Can operate in rural challenging environment | Fragile, not robust |
| [4] | Use of volume holographic phase grating | Lower cost, compact, rugged | Ruled grating |
| [5] | Faraday rotator mirror in reference arm | Lower cost, compact, rugged | Glass mirror mounted in air |
| [6] | Dynamic polarization control not needed due to Faraday mirror above. | Ease of use, patients and clinicians save valuable time | Dynamic polarization control needed. |

An example lens assembly is described below (not as a limitation), but other lens assemblies could be used. The OCDR-OCT system can be adapted to measure retina by collimating the beam exiting the sample arm fiber, expanding the beam using a lens, shrinking the beam to project on the cornea, and the cornea and lens system of the eye will automatically focus the beam on the retina.

Figure 3:
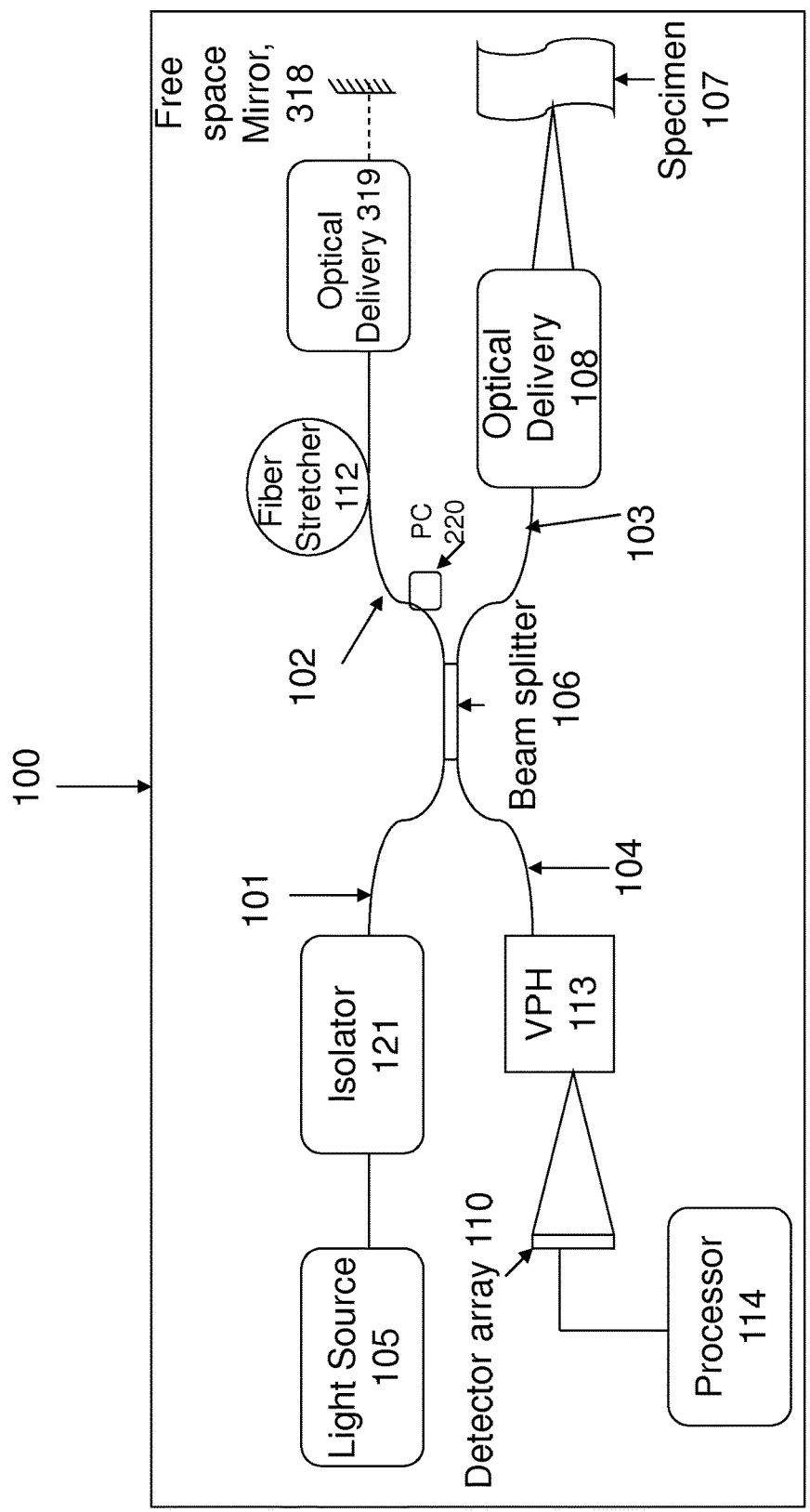
FIG. 3 is a block diagram of the OCDR-OCT system 100 similar to that in FIG. 2 except that the fiber optically integrated mirror is replaced by a free space mirror.

In another variation of this embodiment (FIG. 3), the fiber optically mirror can be replaced by a free space mirror 318. The light can be delivered to the mirror using optical delivery unit 319. FIG. 3 has standard free-space-mirror 318 in the reference arm, which still permits use of instant algorithms such as frequency resampling, dispersion compensation, and Doppler processing algorithms.

Figure 4:
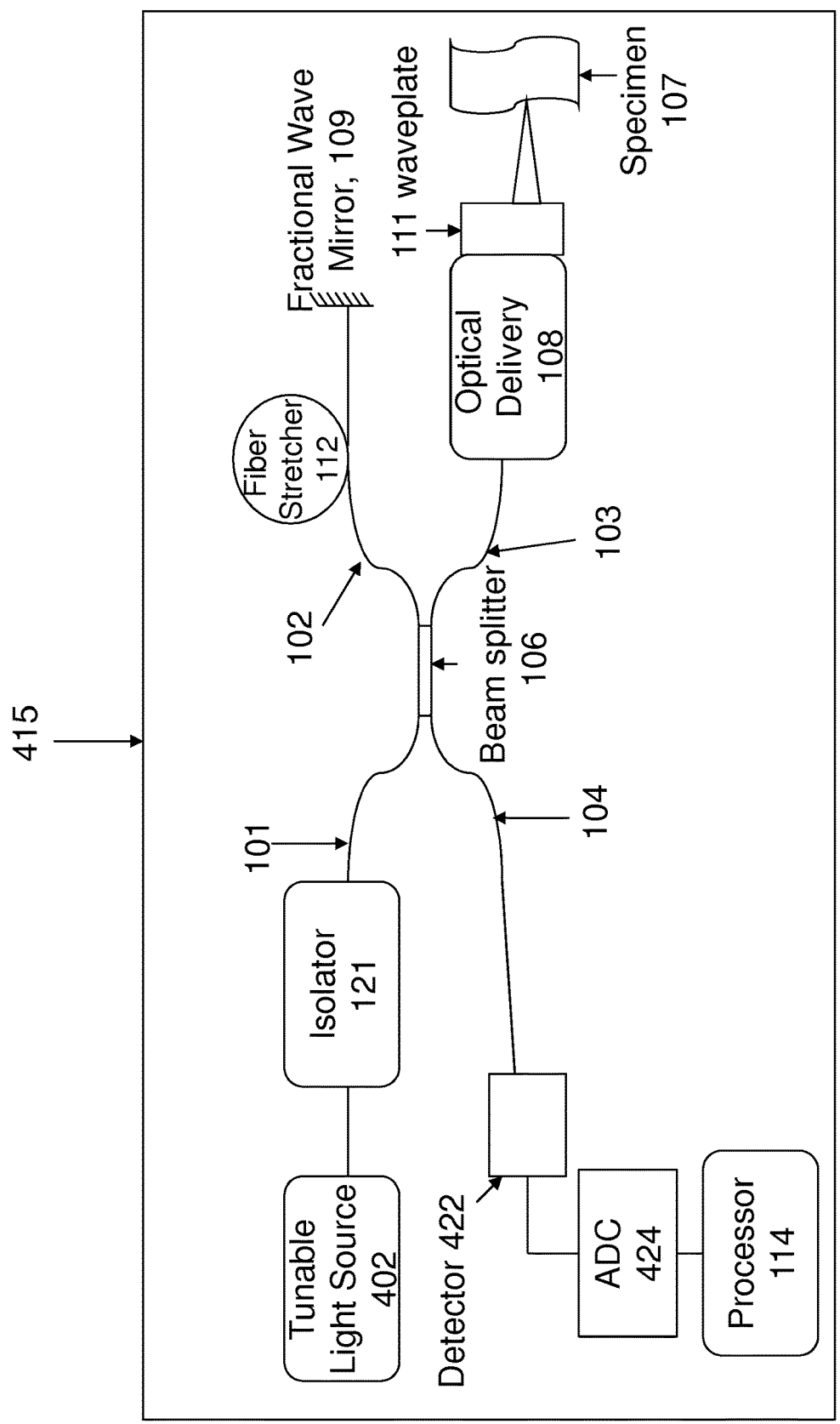
FIG. 4 is a block diagram of the OFDR-OCT system 415 similar to that in FIG. 1 except that the broad-band source is replaced by a tunable frequency source, detector array is replaced by a single high-speed detector, and the diffraction grating is eliminated. Such a system is called swept-source OFDR/OCT.

Frequency Domain OCT or Optical Frequency Domain Reflectometry: In some OCT systems such as frequency domain OCT or Optical Frequency Domain Reflectrometry (OFDR), the broad-band light source is replaced by a tunable frequency light source. The detector array is replaced by a single detector. The use of VPH is not needed for this invention. In this embodiment of instant embodiment (FIG. 4), a fiber-optically integrated Fractional wave mirror 109 in the reference arm 102 of the OFDR-OCT system 415 can be used. Since the polarization of the retro reflected light is orthogonal to the incident light, fiber birefringence effects effectively get cancelled in the reference arm 102. FIG. 4 is another preferred embodiment of instant invention, which applies the use of fractional wave mirror 109, and fiber optic $\lambda/8$ waveplate 111 for optical Frequency domain reflectometry (OFDR)-OCT system 415 and method. Tunable light source 402 in this embodiment is applicable to FIGS. 4 and 7 only. The center wavelength most ideal for the retinal applications range from 750 nm till 1050 nm. The wavelength of the source is tuned very rapidly (e.g., at a rate of 10 kHz 1 MHz) within a spectral range of typically 10 to 100 nm around the center wavelength. The average power of such a source typically ranges from 0.1 mW to 20 mW depending upon the applications. The source may be electrically operated. The existing commercially available sources operate on 110/220V 50/60 Hz power input. In future, these could be operated using lower voltages and battery operated while in transit. ADC 424 is added so that the electrical current is transformed.

In this embodiment there is no VPH 113 and detector array. Instead a Detector 422 is added. It is a photo-diode (which converts light into electricity). The detectors for 300-1000 nm are typically made up of silicon. The detectors for 900-1700 nm are typically made up of InGaAs. These are high-speed detectors with typically 0 to a few hundred MHz bandwidth. It is typically followed by a high-speed A/D (analog to digital) converter, e.g., 8-bit or 12-bit with a conversion rate of 1 to 500 Mega Samples/second. Typical responsivity of photodiodes is 0.1-1 mA/mW. The output voltages are typically −5 to 5V, with typical 50Ω impedance. These assist in achieving typical line-rates (rate of acquisition of A-scans) of 10000 lines/s to 40000 lines/s. The output of the A/D converted is typically directed to the computer using an Ethernet cable (e.g., Gigabit Ethernet) or a USB (typically 2.0 or 3.0) cable, or directly attached to a computer's PCI (Peripheral Controller Interface) bus etc.

FIG. 5 is another embodiment where everything is the same as FIG. 1, except the $\lambda/8$ waveplate is replaced by the polarization compensator (PC) 220. This is a simplified system.

Figure 6:
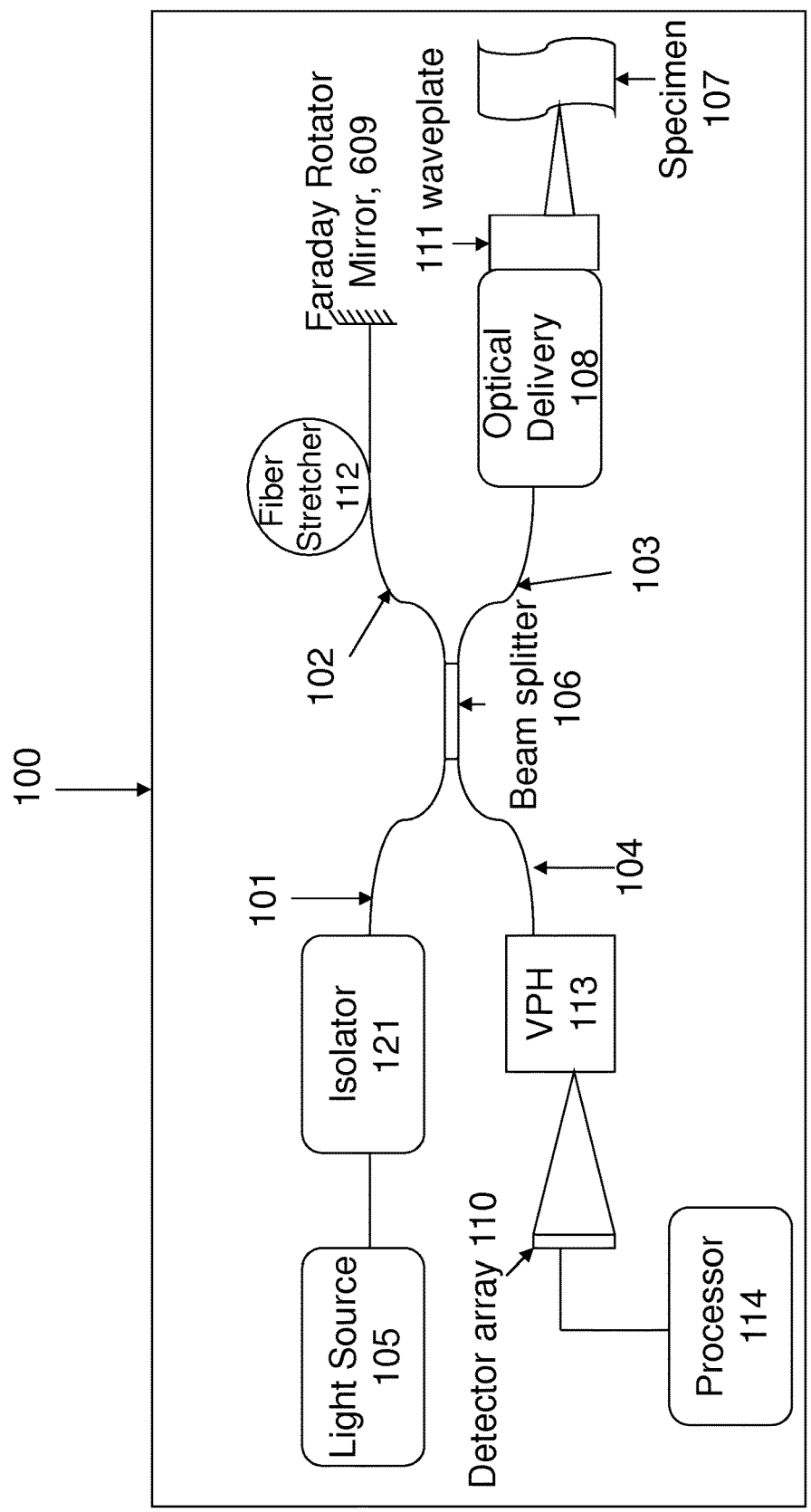
FIG. 6 is a block diagram of the OCDR-OCT system 100 similar to that in FIG. 1 except that the Fractional Wave mirror is replaced by a fiber optically integrated Faraday Rotator Mirror.

FIG. 6 is an embodiment similar to that in FIG. 1 except that the Fractional Wave mirror 109 is replaced by a fiber optically integrated Faraday Rotator Mirror 609, which is an off-the-shelf part. Faraday rotator mirror: The device consists of a fiber-optic mirror preceded by a 45 degrees ($\lambda/8$) Faraday rotator. The polarization of light incident on the Faraday rotator is rotated by 45 degrees, and is directed to the mirror. The reflected light is further rotated by 45 degrees by the Faraday rotator and hence the resulting polarization is orthogonal to incident polarization. We will use the term fiber optically integrated birefringent reference mirror to indicate a fiber optically integrated Faraday Rotator Mirror or a fractional wave mirror.

A Faraday rotator mirror 609 consists of a magnet. It changes the polarization of light by Faraday effect. The polarization of light is affected in the presence of a magnetic field if it is applied parallel to the direction of propagation. Therefore, a Faraday rotator consists of a magnet to generate magneto-optical effect. A Faraday rotator works because one of the components of polarization of propagating light is in ferromagnetic resonance with the material, which causes the phase velocity of the resonating polarization to be higher than the phase velocity of the corresponding orthogonal polarization.

Figure 7:
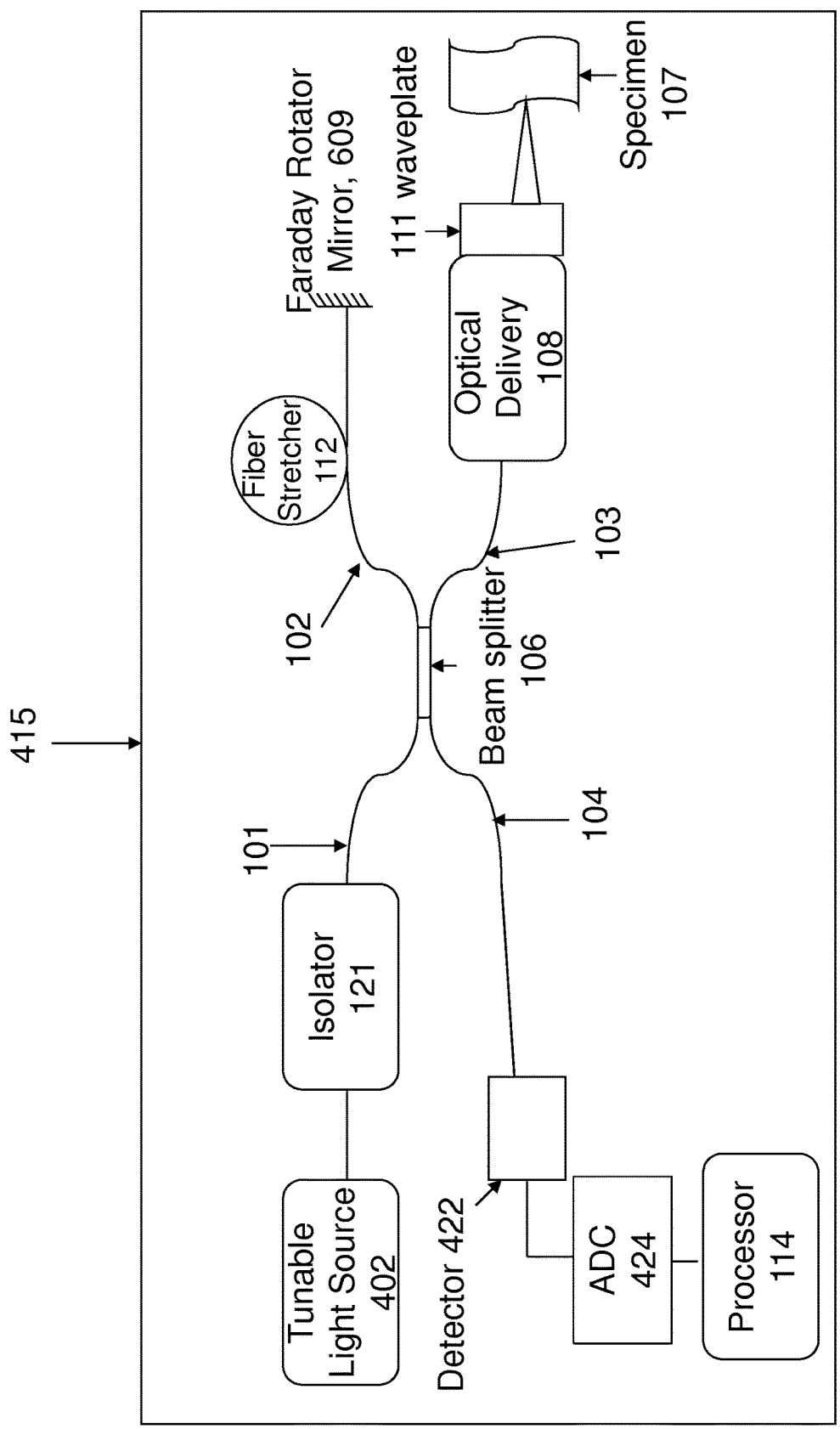
FIG. 7 is a block diagram of the OFDR-OCT system 415 similar to that in FIG. 4 except that the Fractional Wave mirror is replaced by a fiber optically integrated Faraday Rotator Mirror.

FIG. 7 is an embodiment similar to that in FIG. 4 except that the Fractional Wave mirror 109 is replaced by a fiber optically integrated Faraday Rotator Mirror 609, which is an off-the-shelf part. A detector 422 is added.

Figure 8:
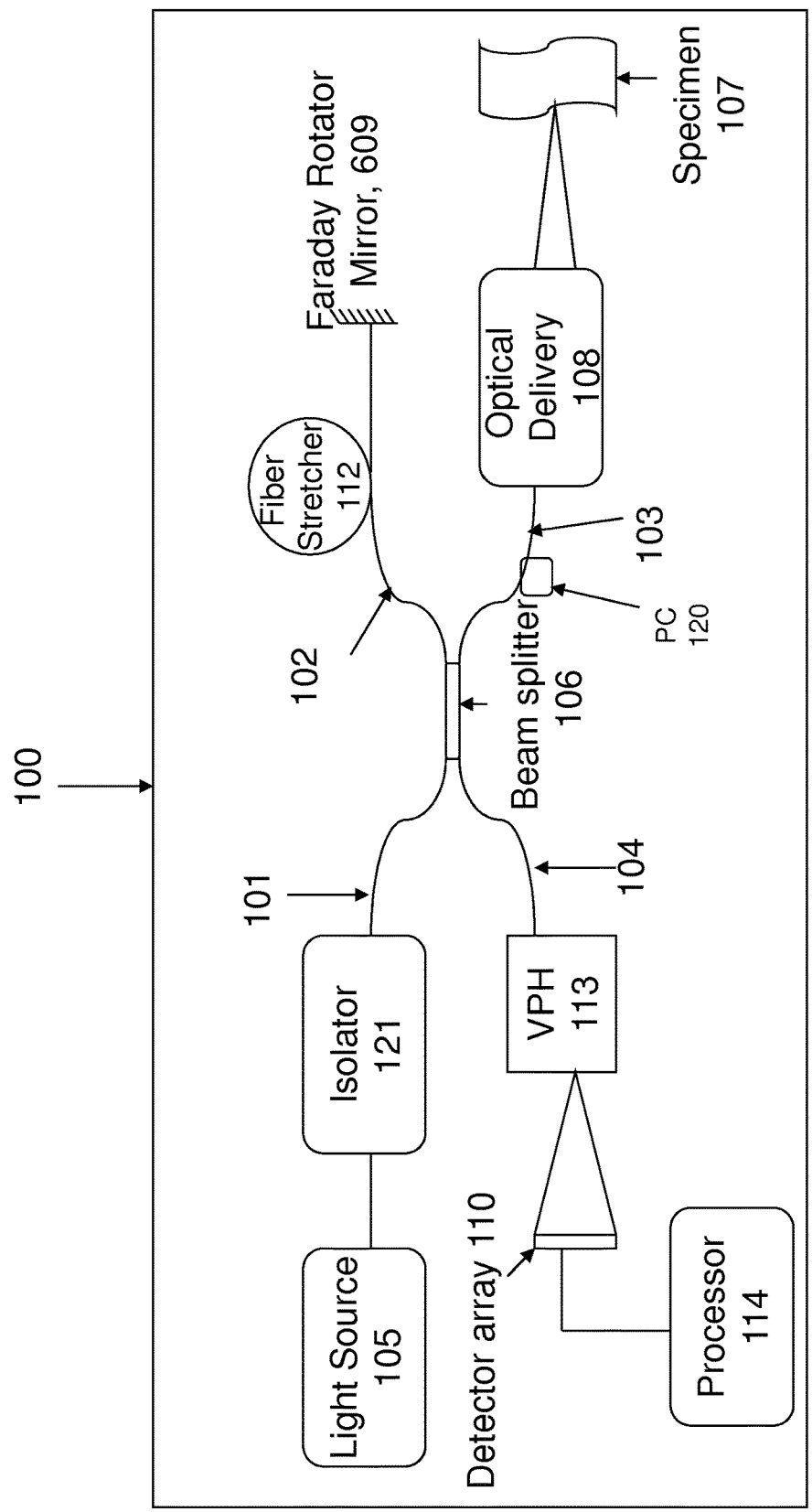
FIG. 8 is a block diagram of the OCDR-OCT system 100 similar to that in FIG. 5 except that the Fractional Wave mirror is replaced by a fiber optically integrated Faraday Rotator Mirror.

FIG. 8 is an embodiment similar to that in in FIG. 5 except that the Fractional Wave mirror 109 is replaced by a fiber optically integrated Faraday Rotator Mirror, which is an off-the-shelf part.

Method of Image Acquisition and Analysis

Figure 9:
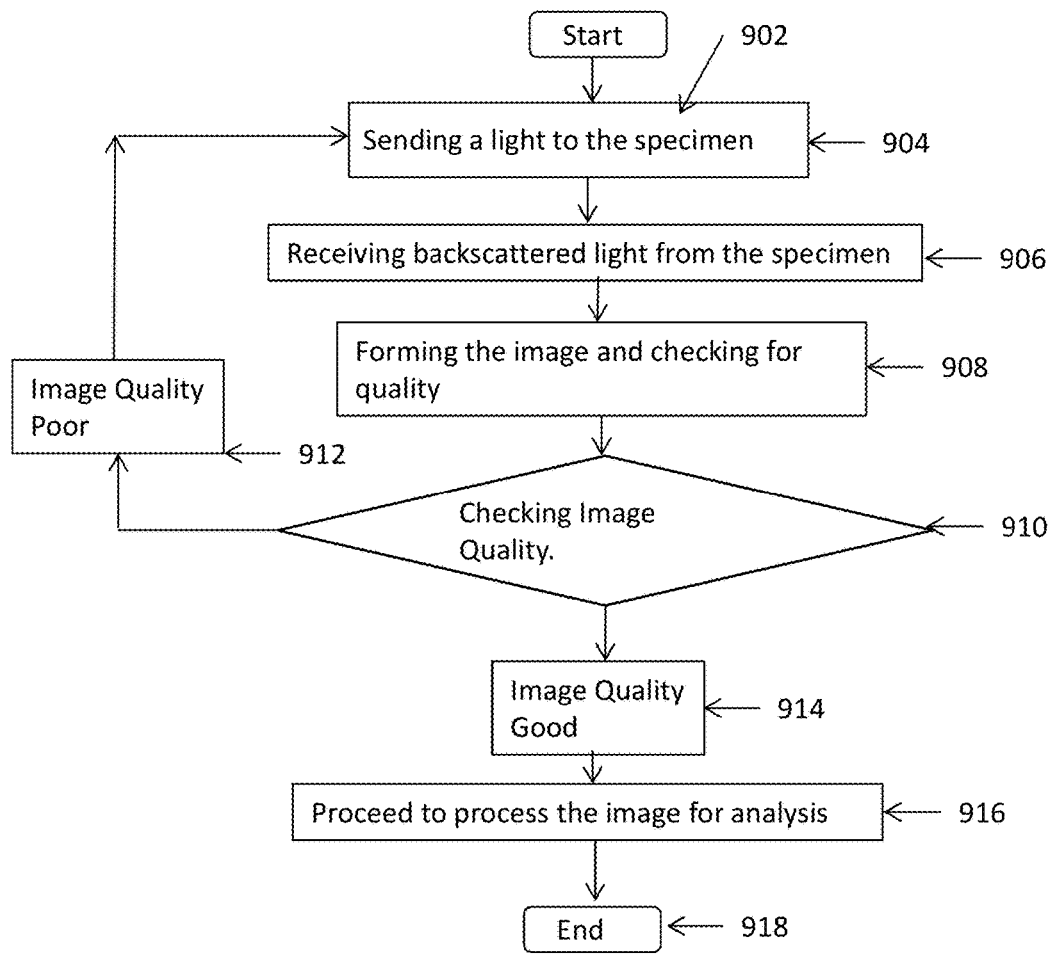
FIG. 9 is a flow chart of describes a method of acquiring an image from a specimen using the OCDR-OCT system.

FIG. 9 describes a method of acquiring an image from a specimen using the OCDR-OCT system. A light source may be a tunable light source, a broadband source, a laser. An apparatus or system is used to send a specific bandwidth light from a light source to a specimen 904 using a source arm and sample arm. A backscattered light from the specimen is received 906 by the optical delivery unit and/or λ/8 plate in one embodiment. An image is formed 908 after going through the VPH and detector array and checked for quality 910. If the image quality is poor 912 the steps from 904 are repeated. If the image quality is good 914 data is further sent to produce an image for analysis 916 using the processor algorithms. The process ends once the image is formed 918.

Figure 10:
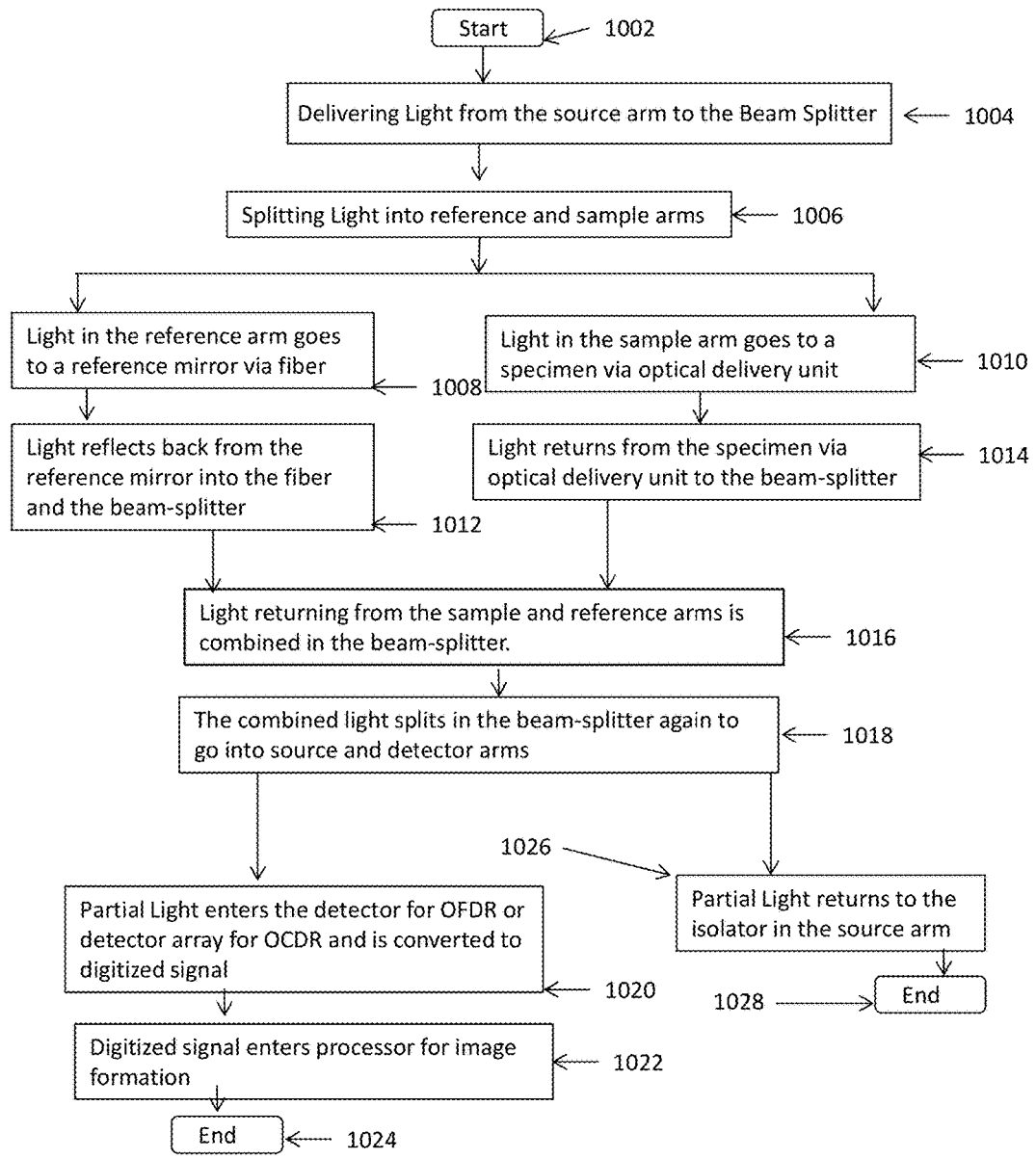
FIG. 10 is a flow chart of method of using the apparatus.

FIG. 10 describes the steps of light travelling through the source to the specimen and the signal from the light being processed. Light is being delivered using a light source using the sample arm to the beam splitter 1004. Beam splitter splits the light into two parts sending the first path light to reference arm 1008 and second path light into the sample arm 1010. The second path light goes to the specimen via the optical delivery unit. The specimen in this case may be retina of the eye for a diabetic patient. Since the blood flows at irregular intervals and the picture is not static at times; stationary-object light-backscattering, moving-object-light-backscattering and combined-object-light-backscattering is returned to the beam splitter.

Sample arm sends the second path of light to the specimen and the specimen reflects back the second path of light as a returning light via the optical delivery unit and the waveplate to the beam splitter 1014. A fiber optically integrated birefringent mirror (reference mirror) returns the light into the fiber to be combined with the returning light from the specimen at the beam splitter 1016. The combined light splits in the beam splitter again to go into source and detector arms 1018. A partial returning light from the beam splitter travels through a detector arm to a volume-phase holographic grating unit and a detector array in OCDR-OCT system or enters the detector if it is OFDR-OCT system to be converted to digitized signal 1020. Digitized signal enters the processor for image formation 1022. The method ends there 1024. On the other hand partial light returns to the isolator using the source arm 1026 and the method ends there 1028.

FIG. 11 shows a high level flow of the processing algorithms. Step 1102 is the beginning step. For the OCDR-OCT system, the spectra are acquired from the detector array as explained earlier (Step 1104). Since the acquired spectra are typically spaced in equal intervals of wavelength, in the step 1106, the spectra are resampled at equal intervals of spatial frequency (k-space) using a frequency resampling algorithm. Next in step 1108, demodulation, which includes inverse Fourier transforming, is performed to extract the complex envelope of the signal. Next in order to correct for the dispersion in the system, the dispersion compensation is performed in step 1110. Next in step 1112, Doppler processing is performed to extract velocity images. The method ends in step 1114. These algorithms are processed in a processor 114 and displayed as a gray scale or pseudo-color image. By way of example, not by limitation, this processor can be a computer, Field Programmable Gate Array (FPGA), an embedded system or a microcontroller.

Frequency Resampling:

The spectra $W_{ccd}(\lambda,x)$ measured by the spectrometer (i.e., the output of the digital array) are equally spaced in wavelength ($\lambda$). However in order to obtain an accurate A-scan measurement by inverse Fourier transforming, the spectra need to be re-measured at equal intervals of spatial frequency ($k=1/\lambda$). Thus, if N is the total number of samples, the spectra are measured at equal intervals in wavelength $\delta\lambda=(\lambda max-\lambda min)/N$. The spectra need to be equally spaced in k-space. Thus, if the corresponding maximum and minimum wavenumbers are kmax=1/λmin and kmin=1/kmax, then the spectra need to be re-sampled at equal intervals in k given by $\delta k=(kmax-kmin)/N$ to obtain $S_{ccd}(k,x)$. If the data are over-sampled while re-sampling by a factor of X, then $\delta k=(kmax-kmin)/XN$.

There are many algorithms for re-sampling the spectra. One such method is simple linear interpolation as described by [Vergnole et al 2010]. Thus, if we need to calculate the spectrum $S_{ccd}(k_0,x)$ at a location $k_0$, and the spectra are measured at the nearest neighboring wavenumbers $k_u$ (upper wavenumber=$1/\lambda_u$, $\lambda_u$ is the upper wavelength), $k_1$ (lower wavenumber=$1/\lambda_1$, $\lambda_1$ is the lower wavelength) Then $S_{ccd}(k_0)=S_{ccd}(k_l)+U_0[S_{ccd}(k_u)-S_{ccd}(k_l)]$;

$$U_0 = \frac{k_0 - k_l}{k_u - k_l}$$

and note that $S_{ccd}(k_l)=W_{ccd}(\lambda_l,x)=$ and $S_{ccd}(k_u)=W_{ccd}(\lambda_u,x)$ Another method described by [Vergnole et al. 2010] is spline interpolation. A preferred and faster method of interpolation is achieved by convolution using a Kaiser-Bessel window as described by [Vergnole et al. 2010].
$S_{ccd}(k_0)=\Sigma_{l=-M/2}^{M/2} S_{ccd}(k_l)C_0(k_l)$ where $k_l$ are the non-linearly placed neighboring values of wavenumbers, M is the size of the convolution kernel. M can be any value, however a value between 3 to 9 can yield good results.

$$C_0(k_l) = \frac{I_0\left(\gamma\sqrt{1-\left(\frac{2H}{M}\right)^2}\right)}{M}$$

where $$H = \text{smaller of } \frac{M}{2} \text{ or } (k-k_l)/\delta k$$

and $I_0$ is the zero-order Bessel function of the first kind. To the best of our knowledge, this is the first time a convolution based interpolation method is used for the OCDR/OFDR/OCT system in which, the polarization issues are solved by using a fiber optically integrated birefringent mirror in the reference arm.

Next in FIG. 12, we present novel algorithm such as demodulation algorithm (step 1202), which is also instant version of the modified Hilbert transform algorithm:
1) Resampled CCD spectra $S_{ccd}(k,x)$ are obtained as a function of k (wavenumber) and lateral dimension x (step 1204).
2) Spectra are Fourier transformed in lateral dimension to obtain spectra $P_{ccd}(k,u)$ where u is frequency in lateral dimension (step 1206).

3) The negative frequency signals are zeroed out using Heaviside function H(u) to provide P'$_{ccd}$(k,u) (step 1208).
4) The P'$_{ccd}$(k,u) is inverse Fourier transformed to obtain complex spectra S'$_{ccd}$(k,x) (step 1210).
5) S'$_{ccd}$(k,x) is inverse Fourier transformed in k (i.e., depth) dimension to obtain complex envelop in Eq. 2 (step 1212)

$$s(z,x)=A(z,x)\exp[-j(2\pi f_s(z,x)zT/D+\varphi(z,x))]. \quad \text{(Eq 6)}$$

Here A(z,x) is the amplitude of the detected signal corresponding to the depth-resolved reflectivity obtained in conventional OCT imaging and $\varphi(z,x)$ is the phase corresponding coherent interference of backscattered waves, commonly known as speckle. Here z is the depth location, x is the lateral location, D is total depth of A-scan, T is the time taken to acquire an A-scan. For a broadband source, A(z,x) is a highly localized function (e.g., a Gaussian) whose width determines the axial resolution of the OCT image. $f_s$ is Doppler shift in light backscattered from moving objects in the sample. A scatterer in the sample moving with a velocity $V_s$ induces a Doppler shift in the sample arm light by the frequency $$f_s=2V_s[\cos\theta]n_t v_0/c \quad \text{(Eq. 7)}$$

where $\theta$ is the angle between the sample probe beam and the direction of motion of the scatterer, $n_t$ is the local tissue refractive index, $v_0$ is the source center frequency, and c is the light velocity.

Dispersion compensation: Group velocity dispersion needs to be matched between the reference and sample arms irrespective of using the Faraday rotating mirror. In some embodiments of instant invention, dispersion is compensated numerically by flattening the Fourier domain phase of a mirror reflection as explained in [Kulkarni 1999]. Current proposed procedure comprises of:
 a) Measuring the interferogram by placing a mirror in the sample, computing the complex envelope m$_s$(z)=A$_m$(z) Exp(j$\varphi_m$(z)) [Here z is distance in depth, A$_m$ is amplitude and $\varphi_m$ is phase) for the interferogram as described in Kulkarni (1999).
 b) Computing the complex envelope for each interferogram measurement for any desired specimen as described in FIG. 12.
 c) Multiplying the complex envelope by Exp(−j$\varphi_m$(z)) to perform dispersion compensation.

Coherent Deconvolution or complex deconvolution for Dispersion Compensation: Another process known as coherent deconvolution is explained in [Kulkarni 1999]. One of the inventors has invented coherent deconvolution methods to correct for imaging artifacts in OCT. The coherent deconvolution process described in Kulkarni (1999) comprises of
 a) Measuring the interferogram by placing a mirror in the sample, computing the complex envelope m$_s$(z)=A$_m$(z) Exp(j$\varphi_m$(z)) (Here z is distance in depth, A$_m$ is amplitude and $\varphi_m$ is phase) for the interferogram,
 b) Computing the Fourier transform of m$_s$(z) to obtain M$_s$(k), where k is spatial frequency,
 c) Computing the complex envelope s(z,x) for each interferogram measurement for any desired specimen,
 d) Computing the Fourier transform of s(z,x) to obtain S(k,x),
 e) Dividing S(k,x) by M$_s$(k) to obtain S$_1$(k,x),
 f) Multiplying S$_1$(k,x) by a Wiener filter to obtain S$_1$(k,x) and
 g) Computing inverse Fourier transform to obtain dispersion corrected sample measurement s$_2$(z, x).

In FIG. 13, Doppler processing algorithm for high accuracy and high precision velocity estimation is described (step 1302).
The data set resulting from the camera can be processed in the processor 114 by the proposed Doppler algorithm which computes STFT (short time Fourier transforms) in lateral (x) direction (step 1306).

$$\hat{S}(z,x,f)=\sum_{m=-N_x/2}^{N_x/2-1} s(z,(x+m)T)\exp[-j2\pi fmT] \quad \text{(Eq 8)}$$

where $N_x$ is the number of A-scans in the STFT window. Next the peak of the STFT spectrum is estimated (step 1308). Next, the Doppler shift is computed by adaptive centroid algorithm (which computes centroid using the power near the peak of the STFT spectrum) (step 1310). Next, the velocity is estimated using Doppler shifts and Velocity images/maps are generated (step 1312). Step 1314 is the end of Doppler processing. The velocity precision is given by $$V_c^{up}=c/(2N_x Tv_0 n_t \cos\theta) \quad \text{(Eq 9)}$$

Doppler shift algorithm is used for estimating Doppler shifts by computing centroid of the short time Fourier transform spectrum using power near the spectral peak, which is an adaptive centroid algorithm. As we can see, velocity precision is higher with higher T (A-scan acquisition period). Therefore, in order to detect micro-flow (~100 to 800 microns/s speed) in capillaries, by way of example but not by limitation, we can choose an A-scan rate of e.g., 2560 A scans/s. The maximum retinal blood flow velocities typically range to 1-4 cm/s. By way of example but not by limitation, higher velocities can be measured by performing another scan at a much higher speed of 42000 A scans/s. By way of example but not by limitation, from Eq. 4, choosing $N_x$ between 1 to 30, we can measure velocities as low as 15 mm/s to 0.5 mm/s, respectively. By way of example but not by limitation, we can scan retina at 2 different scan rates, viz., 2560 A scans/s and 42000 A scans/s. By way of example but not by limitation, in the first set, we can scan 10 concentric circles centered at the optic disc, each consisting of 100 A-scans, which can be acquired in 4 seconds. By way of example but not by limitation, the second set would be acquired at the same locations, 10 concentric circles, each consisting of 420 A-scans, which can be acquired in 1 s. The scanning may be performed by the disc of the retina by performing concentric circles at a variety of speed. Optical delivery unit in the sample arm creates scan patterns, wherein the scan-pattern comprises of at least two B-scans, each B-scan having its specific A-scan rate.

Thus, we propose scan-patterns comprising of at least two B-scans wherein the first B-scan's A-scan rate is slower than the second B-scan rate.

The scan-pattern can comprise of at least two B-scans, each B-scan having its specific A-scan rate.

This Doppler processing step can used to estimate blood flow velocities for augmenting diagnosis of diabetic retinopathy. By acquiring B-scans at various locations, this can be used to obtain a 3-dimensional map of blood flow velocities or blood vessels in the retina as well as any organ of a human or animal body.

The method of FIG. 11 is also applicable for an OFDR-OCT system. In the OFDR-OCT system, the light entering the detector arm from the beam splitter is incident on the detector and converts to an interferometric electric current or signal. The tunable light source produces a light of various frequencies within a specific bandwidth. This sweeping is performed at a very high speed and the detector is able to measure the interference signal at each of the frequencies. Such a high speed measurement produces a spectrum for further processing (step 1104 in FIG. 11). These spectra are typically measured at equal intervals of wavelength. Therefore, the spectra measured by the detector are processed using a re-sampling algorithm. Thus, the spectra are resampled at equal intervals of spatial frequency (k-space) (step 1106). There are some specialized OFDR-OCT systems where the source is able to sweep the bandwidth at equal intervals of spatial frequency (k-space). In those cases, the resampling algorithm is not needed. Next the signal is demodulated to extract its complex envelope (step 1108). The absolute part of the complex envelope is traditional OFDR-OCT signal. Next, the dispersion compensation is performed so that the signal has better depth resolution and higher fidelity (step 1110). Finally, Doppler processing is performed to obtain velocity images, which has velocity information within various locations within a specimen (step 1112).

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

INDUSTRIAL APPLICATIONS

OCDR-OCT system and apparatus of this instant application is very useful for diagnosis and management of ophthalmic diseases such as retinal diseases and glaucoma etc. Instant innovative OCDR-OCT diagnostic system leverages advancements in cross technological platforms. This enables us to supply the global market a low-cost, portable, robust OCDR-OCT imaging tool, which would be affordable to general physicians, optometrists and other health personnel.

This device can also be used for industrial metrology applications for detecting depth-dependent flow and micron-scale resolution thicknesses.

It is to be understood that the embodiments described herein can be implemented in hardware, software or a combination thereof. For a hardware implementation, the embodiments (or modules thereof) can be implemented within one or more application specific integrated circuits (ASICs), mixed signal circuits, digital signal processors (DSPs), digital signal processing devices (DSPDs), programmable logic devices (PLDs), field programmable gate arrays (FPGAs), processors, graphical processing units (GPU), controllers, micro-controllers, microprocessors and/or other electronic units designed to perform the functions described herein, or a combination thereof.

When the embodiments (or partial embodiments) are implemented in software, firmware, middleware or microcode, program code or code segments, they can be stored in a machine-readable medium (or a computer-readable medium), such as a storage component. A code segment can represent a procedure, a function, a subprogram, a program, a routine, a subroutine, a module, a software package, a class, or any combination of instructions, data structures, or program statements. A code segment can be coupled to another code segment or a hardware circuit by passing and/or receiving information, data, arguments, parameters, or memory contents.

What is claimed is:

1. A system, comprising:
    a light source emitting light of a bandwidth called a first light;
    the first light is sent to a specimen using a source arm and a sample arm;
    a beam splitter to split the first light from the source arm as a first path light to a reference arm and as a second path light to the sample arm;
    a fiber optically integrated fractional wave mirror returning the first path light to the beam splitter to join a returning light from the specimen; wherein the fractional wave mirror comprises of a fiber-optic mirror preceded by a fractional waveplate;
    and the fractional waveplate in the reference arm further comprises of a loop of a fiber with a radius dependent upon a photoelastic coefficient of the fiber;
    wherein the fractional waveplate in the reference arm is a fiber optic $(2M+1)\lambda/8$ waveplate; where $\lambda$ is a center wavelength of the light and M is an integer;
    and the fractional waveplate in the reference arm is located near the fiber-optic mirror;
    an optical delivery unit and a fractional waveplate in the sample arm to receive the second path of light at the sample arm;
    the sample arm sends the second path of light to the specimen to generate a probe beam and the specimen reflects back the second path of light as a returning light via the optical delivery unit and the fractional waveplate in the sample arm to the beam splitter;
    wherein the fractional waveplate in the sample arm is a fiber optic $\lambda/8$ waveplate attached to a rear end of the fiber in the sample arm;
    and the fiber optic $(2M+1)$ $\lambda/8$ waveplate is created by looping the fiber and a radius of the loop is calculated using a formula based on the fiber's photoelastic coefficient and radius and $\lambda$;
    a partial returning light from the beam splitter travels through a detector arm to a grating unit and a detector array;
    the grating unit disperses the partial returning light from the beam splitter and a dispersed light enters the detector array to produce spectra; and
    a processor to process the spectra.

2. The system of claim 1, wherein a specimen is at least one of retina, skin, anterior segment of the eye, gastrointestinal tract, lungs, teeth, blood vessels, subsurface area of semi-conductors, chip manufacturing and sensitive medical equipment.

3. The system of claim 1; wherein the processor uses at least one of frequency resampling, demodulation, dispersion compensation, and Doppler processing algorithms,
    wherein dispersion compensation comprises of coherent deconvolution, wherein the frequency resampling comprises of convolution using a Kaiser-Bessel window, wherein the demodulation comprises of a modified Hilbert transform.

4. The system of claim 3; wherein the Doppler processing algorithm includes short time Fourier transforms computation in a direction lateral to the probe beam.

5. The system of claim 3; wherein a Doppler shift is estimated by computing a centroid of a short time Fourier transform spectrum using power near a spectral peak, which is an adaptive centroid algorithm.

6. The system of claim 3; wherein the Doppler processing algorithm estimates blood flow velocities.

7. The system of claim 1; further comprising:
the optical delivery unit in the sample arm creates scan patterns by scanning the probe beam, wherein the scan pattern comprises of at least two B-scans, each B-scan having its specific A-scan rate; wherein at least two B-scans have different A-scan rates.

8. The system of claim 1 further comprising of a fiber stretcher in at least one of the sample arm and the reference arm.

9. The system of claim 1; wherein an image quality is checked before processing the image for analysis.

10. The system of claim 9; wherein the image quality is improved by performing at least one of adjusting the reference arm length, and focusing the second path light using the optical delivery unit.

11. A system, comprising:
a tunable light source producing a light of various frequencies within a bandwidth called a first light;
the first light is sent to a specimen using a source arm and a sample arm;
a beam splitter to split the first light from the source arm as a first path light to a reference arm and as a second path light to the sample arm;
a mirror returning the first path light to the beam splitter to join a returning light from the specimen; and
an optical delivery unit to receive the second path of light at
the sample arm and send it to the specimen to generate a probe beam and the specimen reflects back the second path of light as a returning light via the optical delivery unit to the beam splitter; a partial returning light from the beam splitter travels through the detector arm to a detector;
the detector to convert the partial returning light from the beam splitter into an electric current;
an analog to digital convertor to digitize the electric current into a digitized electric current; and
a processor to perform a data analysis using a specific algorithm on a digitized electric current to form images of the specimen, wherein the specific algorithm is at least one of resampling, demodulation, dispersion compensation, Doppler processing and inverse Fourier transform; and
the images are created from a sequence of A-scans acquired while scanning the probe beam laterally across the specimen;
wherein the optical delivery unit in the sample arm creates a scan pattern;
wherein the scan pattern comprises of at least two B-scans, each B-scan having its specific A-scan rate; wherein at least two B-scans have different A-scan rates
wherein during a single measurement, a slow scan-rate to measure slower velocity another b-scan with a high a-scan rate to measure higher velocity.

12. The system of claim 11, wherein a specimen is at least one of retina, skin, anterior segment of an eye, gastrointestinal tract, lungs, teeth, blood vessels, subsurface area of semi-conductors, chip manufacturing and sensitive medical equipment.

13. The system of claim 12; further comprising:
a retina scanned by performing concentric circles at more than one speed.

14. The system of claim 11; wherein the Doppler processing algorithm includes Short time Fourier transforms computation in a direction lateral to the probe beam.

15. A method, comprising:
sending a light with a bandwidth from a light source to a specimen using a source arm, and a sample arm;
splitting the light using a beam splitter from the source arm as a first path light to a reference arm and as a second path light to the sample arm;
returning the first path light from a fiber optically integrated Faraday rotator mirror to the beam splitter to join a returning light from the specimen;
receiving the second path light at the sample arm using an optical delivery unit and a $\lambda/8$ waveplate-in-the-sample-arm and sending the second path light to the specimen;
reflecting back the second path light from the specimen as the returning light via the optical delivery unit and the $\lambda/8$-waveplate-in-the-sample-arm to the beam splitter;
transporting a partial returning light from the beam splitter through the detector arm to a grating unit and interfering at a detector array to create an interference;
dispersing the partial returning light from the beam splitter using the grating unit to produce a dispersed light and entering the detector array to produce a light spectrum; and
performing a data analysis using a specific algorithm including at least one of, dispersion compensation and Doppler processing on the light spectrum to form an image of the specimen using a processor;
wherein a complex envelope of a depth resolved reflectivity is computed by processing the light spectrum using a modified Hilbert transform.

16. The method of claim 15, wherein a specimen is at least one of retina, skin, anterior segment of an eye, gastrointestinal tract, lungs, teeth, blood vessels, subsurface area of semi-conductors, chip manufacturing and sensitive medical equipment.

17. The method of claim 16; further diagnosing diabetic retinopathy.

18. The method of claim 16; further generating 3-dimensional maps of at least one of blood flow velocities and blood vessels.

19. The method of claim 15, further comprising:
performing a data analysis using the dispersion compensation algorithm includes a process of coherent deconvolution.

20. The method of claim 15; further comprising Doppler processing by short time Fourier transforms.

* * * * *